US008020428B2

(12) United States Patent  (10) Patent No.: US 8,020,428 B2
Snieder  (45) Date of Patent: Sep. 20, 2011

(54) SYSTEM FOR AND METHOD OF MONITORING PROPERTIES OF A FLUID FLOWING THROUGH A PIPE

(75) Inventor: Roelof K. Snieder, Golden, CO (US)

(73) Assignee: Colorado School of Mines, Golden, CO (US)

( * ) Notice: Subject to any disclaimer, the term of this patent is extended or adjusted under 35 U.S.C. 154(b) by 434 days.

(21) Appl. No.: 12/098,261

(22) Filed: Apr. 4, 2008

(65) Prior Publication Data

US 2008/0245147 A1    Oct. 9, 2008

Related U.S. Application Data

(60) Provisional application No. 60/910,156, filed on Apr. 4, 2007.

(51) Int. Cl.
*G01N 9/00* (2006.01)
*G01N 11/00* (2006.01)
(52) U.S. Cl. .................. 73/32 A; 73/54.41; 73/61.49
(58) Field of Classification Search .............. 73/32 A, 73/54.41, 592, 861.357, 861.351, 861.352, 73/861.354, 861.355, 54.24, 61.49
See application file for complete search history.

(56) References Cited

U.S. PATENT DOCUMENTS

| 4,164,149 | A |   | 8/1979 | Okubo |
| 4,739,646 | A |   | 4/1988 | Van Brederode |
| 4,901,575 | A |   | 2/1990 | Bohannan et al. |
| 5,038,614 | A | * | 8/1991 | Bseisu et al. ............... 73/592 |
| 5,594,239 | A |   | 1/1997 | Lessing |
| 5,715,213 | A |   | 2/1998 | Allen |
| 5,748,491 | A |   | 5/1998 | Allison et al. |
| 5,790,473 | A |   | 8/1998 | Allen |
| 5,799,900 | A |   | 9/1998 | McDonnell |
| 6,289,289 | B1 |   | 9/2001 | Zweifel |
| 6,487,914 | B1 |   | 12/2002 | Hodge |
| 6,556,288 | B1 |   | 4/2003 | Chovan |
| 6,564,156 | B2 |   | 5/2003 | Kuo et al. |
| 6,647,161 | B1 |   | 11/2003 | Hodge |
| 6,807,862 | B2 |   | 10/2004 | Duron et al. |
| 7,162,915 | B2 | * | 1/2007 | Drahm et al. ............. 73/54.24 |
| 7,228,240 | B2 |   | 6/2007 | Duron et al. |
| 7,509,219 | B2 | * | 3/2009 | Henry et al. .................. 702/50 |

(Continued)

OTHER PUBLICATIONS

Office Action dated Aug. 5, 2008, U.S. Appl. No. 11/406,685, 14 pages.

(Continued)

*Primary Examiner* — Jacques M Saint Surin
(74) *Attorney, Agent, or Firm* — Dorsey & Whitney LLP

(57) ABSTRACT

A system and method for determining a fluid property for a fluid flowing in a pipe may include sensing baseline vibrations when test fluids with known values for a fluid property (e.g., fluid density or fluid viscosity) flow through the pipe, or computer modeling the baseline vibrations. The baseline vibrations are analyzed via cross-correlation and/or deconvolution to separate the fluid filled pipe's baseline combined structural response from excitation and base coupling effects. During field or other operations, sensors may take vibrational readings along the pipe when an operational fluid (e.g., drilling fluid) flows through the pipe. The operational vibrations may be analyzed via cross-correlation and/or deconvolution to separate the operational combined structural response of the fluid filled pipe from excitation and base coupling effects. The baseline and operational structural responses may compared. Similarities or differences in the structural responses may be used to determine fluid properties of the operational fluid.

5 Claims, 17 Drawing Sheets

U.S. PATENT DOCUMENTS

| | | | | |
|---|---|---|---|---|
| 7,520,162 | B2* | 4/2009 | Wenger et al. | 73/54.41 |
| 7,526,966 | B2* | 5/2009 | Gysling et al. | 73/861.23 |
| 7,549,319 | B2* | 6/2009 | Headrick | 73/32 A |
| 2006/0248954 | A1 | 11/2006 | Snieder | |
| 2009/0296086 | A1* | 12/2009 | Appel et al. | 356/326 |

OTHER PUBLICATIONS

Amendment and Response to Office Action filed Feb. 4, 2009, U.S. Appl. No. 11/406,685, 6 pages.

Office Action dated May 7, 2009, U.S. Appl. No. 11/406,685, 8 pages.

Aki, K., et al., *Quantitative Seismology*, University Science Books, Sausalito, CA, 2nd edition, 10 pages, 2002.

Backus, M.M., "Water reveberations—their nature and elimination," *Geophysics*, vol. XXIV, No. 2, pp. 233-261, 1959.

Baek, et al., "Elevators as an Excitation Source for Structural Health Monitoring in Buildings," 4th World Conference on Structural Control and Monitoring, La Jolla, California, Jul. 2006, pp. 1-8.

Derode, A., et al., How to estimate the Green's function for a heterogeneous medium between two passive sensors? Application to acoustic waves, *Appl. Phys. Lett.*, vol. 83, No. 15, pp. 3054-3056, 2003.

Kalisvaart, et al., Correction to the [Backus] Paper "Water reveberations—their nature and elimination," Geophysics, vol. XXVI, Nos. 1-6, p. 242, 1961.

Lobkis, O.I., et al., "On the emergence of the Green's function in the correlations of a diffuse field," *J. Acoust. Soc. Am.*, vol. 110, No. 6, pp. 3011-3017, 2001.

Masri, et al., "Application of a Web-enabled real-time structural health monitoring system for civil infrastructure systems," *Smart Materials and Structures*, vol. 13, 2004, pp. 1269-1283.

Nigbor, et al., "New Developments in Health Monitoring for Civil Structures," *Strong Motion Instrumentation for Civil Engineering Structures*, M. Erdik et al. (eds.), Kluwer Academic Publishers, 2001, 9 pages.

Nigbor, et al., "Feasibility of Detecting Known Structural Changes from Ambient Bridge Vibration Data," *Structural Health Monitoring—The Demands and Challenges*, Fu-Kuo Chang (ed.), CRC Press 2001, 9 pages.

Riley, D.C., et al., "2-D multiple reflections," *Geophysics*, vol. 41, No. 4, pp. 592-620, 1976.

Snieder, R., "Extracting the Green's function for the correlation of coda waves: a derivation bases on stationary phase," *Phys. Rev. E.*, 69:046610, 8 pages, 2004.

Snieder, R., et al., "Spurious multiples in seismic interferometry of primaries," *Geophysics*, vol. 71, No. 4, pp. 111-124, 2006.

Snieder, R., *A Guided Toure of Mathematical Methods for the Physical Sciences*, Cambridge Univ. Press, Cambridge, UK, 2nd edition, 8 pages, 2004.

Snieder, R., et al., "Equivalence of the virtual source method and wavefield deconvolution in seismic interferometry," Phys. Rev. E., vol. 73, 9 pages, 2006.

Snieder, R., et al., "Extracting the Building Response Using Seismic Interferometry: Theory and Application to the Millikan Library in Pasadena, California," Bulletin of the Seismological Society of America, vol. 96, No. 2, pp. 586-598, Apr. 2006.

Trampert, J., et al., "SH propagator matrix and Qs estimates from borehole- and surface-recorded earthquake data," *Geophys. J. Int.*, vol. 112, pp. 290-299, 1993.

Wapenaar, K., "Retrieving the elastodynamic Green's function of an arbitrary inhomogeneous medium by cross correlation," *Phys. Rev. Lett.*, 93:254301, 4 pages, 2004.

Wapenaar, K., et al., "Relations between reflection and transmission responses of three-dimensional inhomogeneous media," *Geophys. J. Int.*, vol. 156, pp. 179-194, 2004.

Amendment Response to Office Action dated Sep. 8, 2009, U.S. Appl. No. 11/406,685, 9 pages.

Final Office Action dated Dec. 24, 2009, U.S. Appl. No. 11/406,685, 11 pages.

Non-final Office Action, U.S. Appl. No. 11/406,685, 8 pages, Mar. 2, 2011.

Amendment and Response to Non-Final Office Action, U.S. Appl. No. 11/406,685, 9 pages, Jan. 24, 2011.

\* cited by examiner

VERTICAL CROSS SECTION OF THE MILLIKAN LIBRARY IN THE NORTH-SOUTH DIRECTION.

FLOOR PLAN OF THE MILLIKAN LIBRARY. ON FLOORS 1-9 SEISMOMETERS MEASURE THE MOTION IN TWO HORIZONTAL DIRECTIONS ON THE WEST SIDE OF THE BUILDING, AND THE NORTH-SOUTH MOTION ON THE EAST SIDE, AS INDICATED BY THE ARROWS.

THE NORTH-SOUTH COMPONENT OF THE MOTION IN THE WEST SIDE OF THE MILLIKAN LIBRARY RECORDED IN THE BASEMENT (B) AND THE FLOORS INDICATED BY THE NUMBERS NEXT THE DIFFERENT TRACES.

THE WAVEFORMS OF FIG.3 AT THE DIFFERENT FLOORS AFTER DECONVOLUTION WITH THE WAVES RECORDED IN THE BASEMENT

THE WAVEFORMS OF FIG.3 AT THE DIFFERENT FLOORS AFTER DECONVOLUTION WITH THE WAVES RECORDED AT THE TOP FLOOR.

THE WAVEFORMS OF FIG.3 AT THE DIFFERENT FLOORS AFTER DECONVOLUTION WITH THE WAVES RECORDED IN THE BASEMENT.

THE WAVEFORMS OF FIG.3 AT THE DIFFERENT FLOORS AFTER DECONVOLUTION WITH THE WAVES RECORDED IN THE TOP FLOOR.

THE LOCATION OF THE POLES IN THE COMPLEX $\omega$ - PLANE AND THE CONTOUR INTEGRATION THAT IS USED FOR $t > (2H - z)/c$.

THE ARRIVAL TIMES OF THE UPGOING AND DOWNGOING WAVES IN FIG.5.

THE NATURAL LOGARITHM OF THE RATIO OF THE AMPLITUDES OF THE UPGOING AND DOWNGOING WAVES OF FIG.5 AS A FUNCTION OF THE TWO-WAY DISTANCE TO THE TOP OF THE BUILDING.

THE NATURAL LOGARITHM OF THE ENVELOPE OF THE DECONVOLVED WAVES IN FIG.4 AFTER APPLYING A BANDPASS FILTER WITH CORNER FREQUENCIES OF 1 Hz AND 3 Hz, RESPECTIVELY.

THE WAVEFORMS OF FIG.3 AT THE DIFFERENT FLOORS AFTER CORRELATION WITH THE WAVES RECORDED IN THE BASEMENT.

THE WAVEFORMS OF FIG.3 AT EVERY FLOOR DECONVOLVED WITH THE UPGOING WAVE IN THE BASEMENT.

THE WAVEFORMS OF FIG.3 AT EVERY FLOOR DECONVOLVED WITH THE DOWNGOING WAVE IN THE BASEMENT.

THE WAVEFORMS OF FIG.13 (THICK LINES) SUPERPOSED THE TIME-REVERSED VERSION OF THE WAVEFORMS OF FIG.14 (THIN LINES).

THE WAVEFORMS OF FIG.15 AT EVERY FLOOR AFTER MULTIPLICATION WITH EXP($-t/\tau$) (THICK LINES) AND EXP ($+t/\tau$) (THIN LINES), RESPECTIVELY USING $\tau$ = 1.4 S.

SYSTEM FOR AND METHOD OF MONITORING PROPERTIES OF A FLUID FLOWING THROUGH A PIPE

CROSS REFERENCE TO RELATED APPLICATIONS

This application claims under 35 U.S.C. §119(e) the benefit of U.S. Provisional Application No. 60/910,156, titled "System For And Method Of Monitoring Properties Of A Fluid Through A Pipe" and filed on Apr. 4, 2007, which is hereby incorporated herein by reference in its entirety.

INCORPORATION BY REFERENCE

This application is related to and incorporates herein by reference in its entirety U.S. Provisional Application 60/675,363, which was filed Apr. 26, 2005 and entitled "A System For And Method Of Monitoring Structural Integrity Of A Structure." The present application is also related to and incorporates herein by reference in its entirety U.S. patent application Ser. No. 11/406,685, which was filed Apr. 19, 2006 and entitled "System for and Method of Monitoring Structural Integrity of a Structure."

FIELD OF THE INVENTION

The present invention relates to systems and methods for monitoring the properties of a fluid passing through a fluid conveying pathway. More specifically, the present invention relates to systems and methods for determining the fluid density of a fluid flowing through a pipe.

BACKGROUND OF THE INVENTION

Natural disasters (e.g., hurricanes, tornadoes, earthquakes, etc.), man-caused disasters (e.g., accidents and terrorist attacks), deferred maintenance, heavy and/or long term use, exposure to corrosive elements/conditions, and age are just some of the factors that can bring about structural degradation of the structural framework of buildings, towers, bridges, dams, cranes, etc. It is often difficult to determine whether the structural framework of a building, crane, etc. is still structurally sound after a long service period or after being subjected to a structurally traumatic event.

Fluids flow through a fluid conveying pathway, for example, an open channel, closed conduit, etc. (referred to generically as a pipe throughout the rest of this document). Often it is desirable to obtain information regarding the properties (e.g., viscosity, fluid density, etc.) of the fluid flowing through the pipe. However, access to the fluid for measurement or monitoring purposes may be limited or nonexistent due to the fluid being enclosed or the pipe being in an inaccessible location.

There is a need in the art for a system for, and a method of, determining the existence of structural change in a structural framework. There is also a need in the art for a system for, and method of, determining the properties of a fluid flowing through a pipe.

BRIEF SUMMARY OF THE INVENTION

The present invention, in one embodiment, is a system for determining the structural change (e.g. structural degradation) of a structural framework coupled to a support base, wherein the structural framework is subjected to first and second periods of excitation. The system comprises a plurality of motion sensors and a CPU. The plurality of motion sensors are distributed on the structural framework. The CPU is in operable communication with the motion sensors.

The plurality of sensors provides to the CPU first motion data that is associated with the first period of excitation. The motion of a structure is a function of the following components or effects: the excitation experienced by the structure; the coupling of the structure to its support base; and the structural response (i.e., the mechanical properties) of the structure.

The CPU deconvolves the first motion data to separate a first structural response from a first excitation effect and a first coupling effect. The first structural response is the response of the structural framework during the first period of excitation. The first excitation effect is the effect caused by the excitation of the first period of excitation. The first coupling effect is the effect of the structural framework being coupled to the support base during the first period of excitation.

The plurality of sensors provides to the CPU second motion data that is associated with the second period of excitation. The CPU deconvolves the second motion data to separate a second structural response from a second excitation effect and a second coupling effect. The second structural response is the response of the structural framework during the second period of excitation. The second excitation effect is the effect caused by the excitation of the second period of excitation. The second coupling effect is the effect of the structural framework being coupled to the support base during the second period of excitation.

The CPU compares the first and second structural responses. A difference between the first and second structural responses means that the structural framework has structurally changed (e.g., structurally degraded).

The present invention, in another embodiment, is a method for determining the structural change (e.g., degradation) of a structural framework coupled to a support base. The method comprises: distributing a plurality of motion sensors on the structural framework; placing the plurality of motion sensors in operable communication with a CPU; providing from the plurality of motion sensors to the CPU first motion data that is associated with a first period of excitation; and using the CPU to deconvolve the first motion data to separate a first structural response from a first excitation effect and a first coupling effect. The first structural response is the response of the structural framework during the first period of excitation. The first excitation effect is the effect caused by the excitation of the first period of excitation. The first coupling effect is the effect of the structural framework being coupled to the support base during the first period of excitation.

In one embodiment, the method further comprises: providing, from the plurality of motion sensors to the CPU, second motion data that is associated with a second period of excitation; and using the CPU to deconvolve the second motion data to separate a second structural response from a second excitation effect and a second coupling effect. The second structural response is the response of the structural framework during the second period of excitation. The second excitation effect is the effect caused by the excitation of the second period of excitation. The second coupling effect is the effect of the structural framework being coupled to the support base during the second period of excitation.

In one embodiment, the method further comprises comparing the first and second structural responses. A difference between the first and second structural responses means that the structural framework has structurally changed (e.g., structurally degraded).

The present invention, in one embodiment, is a method for determining the structural change of a structural framework coupled to a support base. The method comprises comparing a first mechanical property of the structural framework to a second mechanical property of the structural framework. The first mechanical property is associated with, or obtained during, a first time period in the life of the structure. The second mechanical property is associated with, or obtained during, a second time period in the life of the structure.

In one embodiment, at least one of the mechanical properties includes a shear velocity of the framework. In one embodiment, at least one of the mechanical properties includes an attenuation value of the framework. In one embodiment, the method further comprises sensing motion data of the framework caused by excitation of the framework during the first and second time periods. In one embodiment, the method further comprises separating the first and second mechanical properties from the motion data.

The present invention, in one embodiment, is a method for determining at least one aspect of a dynamic response of a structural framework coupled to a support base. The method includes obtaining first motion data associated with a first period of excitation of the structure, and deconvolving the first motion data to compute new wave states of the structural framework that satisfy boundary conditions that are different from the structural framework's actual boundary conditions. In one embodiment, at least one aspect of the dynamic response is a shear velocity or an attenuation value of the structural framework. In one embodiment, deconvolving of the first motion data results in new data that appears as if waves are not reflected off of the support base and/or new data that appears as if waves are not reflected off of portions of the structural framework.

Disclosed herein are methods and systems for determining a fluid property of a fluid flowing through a fluid conveying pathway.

In one embodiment, the method includes: providing an array of sensors along at least a portion of the pathway; placing a CPU in operable communication with the sensors; communicating baseline pathway vibration readings from the sensors to the CPU when a fluid having a known value for the fluid property flows through the pathway; subjecting the baseline pathway vibration readings to deconvolution or cross-correlation to separate a baseline combined structural response of the fluid pathway from excitation and base coupling affects; saving the baseline combined structural response; communicating actual operational pathway vibration readings from the sensors to the CPU when an actual operational fluid flows through the pathway during actual operations; subjecting the actual operational pathway vibration readings to deconvolution or cross-correlation to separate an actual operational combined structural response of the fluid pathway from excitation and base coupling effects; saving the actual combined structural response; comparing the baseline and actual operational structural responses to determine a difference between the responses; and using the difference to determine the fluid property of the actual operational fluid.

In another embodiment, the method includes: obtaining a first vibration reading for a fluid conduit when a first fluid including a known value for a fluid property flows through the fluid conduit; subjecting the first vibration reading to at least one of deconvolution and cross-correlation to separate a first combined structural response of the fluid conduit for the first vibration reading from excitation and base coupling effects for the first vibration reading; obtaining a second vibration reading for the fluid conduit when a second fluid flows through the fluid conduit; subjecting the second vibration reading to at least one of deconvolution and cross-correlation to separate a second combined structural response of the fluid conduit for the second vibration reading from excitation and base coupling effects for the second vibration reading; and determining a value of the fluid property for the second fluid using the first and second combined structural responses.

In yet another embodiment, the method includes: obtaining a first vibration reading for a first fluid conduit including first mechanical properties when a first fluid including a known value for a fluid property flows through the fluid conduit; subjecting the first vibration reading to at least one of deconvolution and cross-correlation to separate a first combined structural response of the fluid conduit for the first vibration reading from excitation and base coupling effects for the first vibration reading; obtaining a second vibration reading for a second fluid conduit including second mechanical properties similar the first mechanical properties of the first fluid conduit when a second fluid flows through the second fluid conduit; subjecting the second vibration reading to at least one of deconvolution and cross-correlation to separate a second combined structural response of the second fluid conduit for the second vibration reading from excitation and base coupling effects for the second vibration reading; and determining a value of the fluid property for the second fluid using the first and second combined structural responses.

In still yet another embodiment, the method includes: obtaining a first vibration reading for a fluid conduit when a fluid flows through the fluid conduit; subjecting the first vibration reading to at least one of deconvolution and cross-correlation to separate a first combined structural response of the fluid conduit for the first vibration reading from excitation and base coupling effects for the first vibration reading; and determining a value of a fluid property for the fluid by using the first combined structural response of the fluid conduit and a second combined structural response for a second vibration reading.

While multiple embodiments are disclosed, still other embodiments of the present invention will become apparent to those skilled in the art from the following Detailed Description, which shows and describes illustrative embodiments of the invention. As will be realized, the invention is capable of modification in various aspects, all without departing from the spirit and scope of the present invention. Accordingly, the drawings and Detailed Description are to be regarded as illustrative in nature and not restrictive.

DETAILED DESCRIPTION

Figure 1:
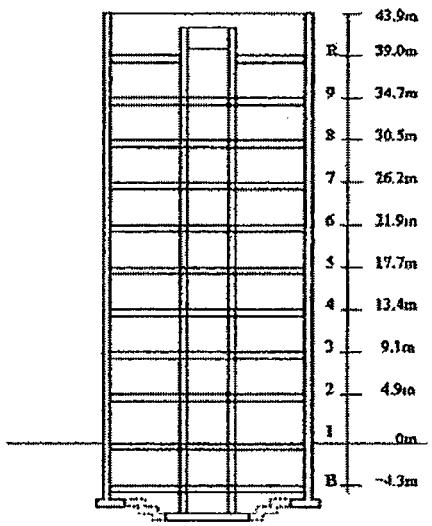
FIG. 1 is a north-south elevation of the building.

I. Introduction.

The response (i.e., motion) of a building caused by natural or man-made shaking is largely a function of the mechanical properties of the building. These mechanical properties include the building's shear wave velocity (i.e., the rate at which shear waves propagate through the building) and the attenuation of the building (i.e., the building's ability to attenuate the wave energy resulting from the natural or man-made shaking). The building's shear wave velocity, together with the geometry of the building, controls the resonant frequencies of the building. The attenuation of the building determines the rate of energy dissipation in the building, which in turn controls the motion of the building for a given excitation.

A complicating factor in the response of a building to shaking is that this response depends both on the properties of the building, as well as on the nature of the coupling to the subsurface. It has been documented that the resonant frequencies of a building can change after heavy precipitation that changes the coupling between the building and the ground with soil-moisture. In order to fully understand the response of the building, one needs to unravel the properties of the building itself from the coupling of the building to the ground.

The combined response of a building and the ground coupling could be retrieved from an impulsive loading of the building. In general, such an impulsive load cannot be applied for practical reasons, and even if it could, the response of the building to this excitation depends on the properties of the building itself, as well as on the ground coupling. This work is aimed at retrieving the building response from the recording of incoherent shaking of the building, and to unravel the properties of the building itself from the coupling of the building to the subsurface.

We analyze this problem using a technique referred to as seismic interferometry. This technique is based on the correlation of wave recorded at different receivers. When the excitation of the waves is evenly distributed in space, or among the normal modes of the system, this correlation can be shown to lead to the Green's function that accounts for the wave propagation between receivers. This technique is valuable as it makes possible the study of the waves that propagate between receivers, without needing a source at one of the receiver locations. It does not matter whether the waves recorded at the receivers are excited by coherent sources or incoherent sources. Here we apply this technique to extract the building response of the Robert A. Millikan Library in Pasadena, Calif. In contrast to earlier work on seismic interferometry, we base our analysis on the deconvolution of the recorded waves at different locations in the building rather than on the correlations.

In Section II of this Detailed Description, we give details on the Robert A. Millikan Library and the employed recordings of the motion of the building. We describe the deconvolution that we use in Section III of this Detailed Description. In Section IV of this Detailed Description, we present a simple analytical model of the motion of the building that is based on interfering upgoing and downgoing waves. We show that the deconvolution gives a response that is independent of the excitation and that it does not depend on the coupling of the building with the ground. We show that these deconvolved waves can be interpreted either as propagating waves or as normal modes. We use the deconvolved waves in Section V of this Detailed Description to determine the shear velocity and the attenuation of the building. In Section VII of this Detailed Description, we use integration in the complex plane to show how the normal modes of the building can be obtained from the deconvolved waveforms. In Section VIII of this Detailed Description, we show that from the recorded response one can infer the response of the structure if it would satisfy different boundary conditions than the real structure does. In Sections IX and X of this Detailed Description, examples of how the methodology presented in the preceding Sections can be applied to actual structures are presented.

II. The Millikan Library and the Recorded Waves.

The Robert A. Millikan Library is a 10-story reinforced concrete building located on the campus of the California Institute of Technology in Pasadena, Calif. Completed in 1967, the building is 21×22.9 m in plan, and 43.9 m high from the ground level. The north-south elevation of the building, and the plans for a typical floor and the foundation are given in FIGS. 1 and 2, respectively. There is a 4.3 m deep basement level below the ground. The structural system includes moment-resisting frames and shear walls. The shear walls at the center of the building form the elevator shaft and carry lateral loads in the north-south direction, whereas the curved shear walls at the north and south ends carry lateral loads in the east-west direction. The foundation system is composed of a central pad 32 feet wide by 4 feet deep that extends between the east and west curved shear walls. In addition, 10 feet wide by 2 feet deep continuous foundation beams run in the east-west direction beneath the columns at the north and south ends of the building. The alluvium under the foundation consists of medium to dense sands mixed with gravels to the bedrock at a distance of about 275 m. The water table is about 11 m deep.

Figure 2:
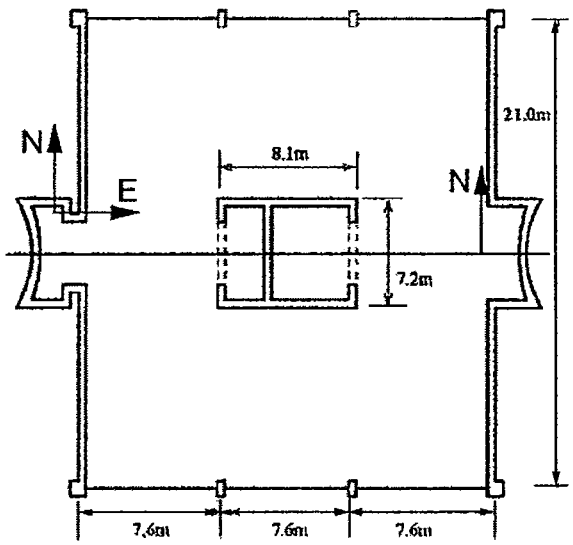
FIG. 2 is a plan view of a typical floor and the foundation of the building depicted in FIG. 1.

The building was first instrumented in 1968 with 2 permanent tri-axial accelerometers located on the roof and the basement. A 10-channel strong motion array was added to the instrumentation in 1979, with channels on the basement, the 6th floor, and the roof. After the 1994 Northridge, Calif., earthquake, the instrumentation was upgraded to a 36-channel, triggered system with three horizontals at each floor plus three verticals in the basement. The locations and directions of these are shown by the arrows in FIG. 2. Specifically, as shown in FIG. 2, on floors 1-9, seismometers measure the north-south motion and the east-west motion on the west side of the building, and the north-south motion on the east side. In 2000, the system was converted to a 19-bit real-time system recording continuously at 200 Hz. Also, a separate 24-bit tri-axial accelerometer was installed on the 9th floor recording continuously as a CISN (formerly TriNet) station MIK. FIG. 2 shows the current sensor layout in the building.

Since its construction, the building has been a field laboratory for researchers in earthquake engineering. A synchronized shaker was permanently installed on the roof of the building in the early 1970's, which is still operational and used for forced vibration testing experiments. A large number of studies on the dynamic behavior of the building have been completed by using vibration data from shaker experiments and real earthquakes.

Figure 3:
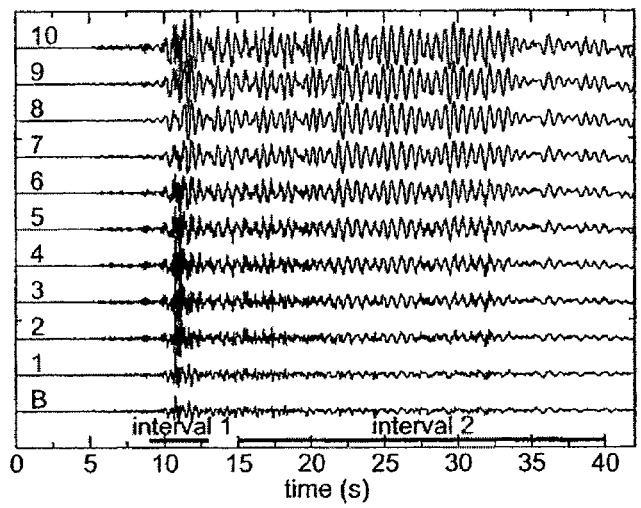
FIG. 3 is a graphical representation of building motion during an earthquake.

The recorded north-south component of the motion in the west side of the building after an earthquake as recorded in basement (B) and the floors indicated by the numbers next to the different traces is graphically represented in FIG. 3. The P-waves generated by the earthquake arrive before t=9 s. These waves couple weakly to the horizontal motion in the building. The S-wave that arrives around t=11 s is the strongest phase. The surface waves that arrive later excite a resonance in the building with an amplitude that increases with the floor level.

III. The Deconvolved Waveforms.

In this study we extract the building response by deconvolving the waves recorded at all floors either with the waveform recorded in the basement, or with the signal recorded at the top floor of the building. The deconvolution of two signals $u_1(\omega)$ and $u_2(\omega)$ is in the frequency domain given by Expression 1, which is:

$$D(\omega) = u_1(\omega)/u_2(\omega)$$

Expression 1 is unstable near the notches in the spectrum of $u_2$ because the denominator goes to zero. In order to stabilize the deconvolution, we instead used the estimator for the deconvolution as provided in Expression 2, which is:

$$D(\omega) = \frac{u_1(\omega)u_2^*(\omega)}{|u_2(\omega)|^2 + \varepsilon},$$

where the asterisk denotes the complex conjugation. When $\epsilon=0$ this expression reduces to Expression 1. In this study the parameter $\epsilon$ was set to 10% of the average spectral power.

Figure 4:
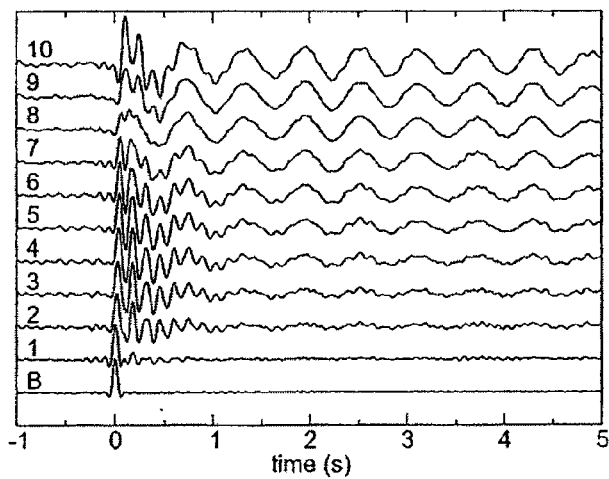
FIG. 4 is a graphical representation of the waveforms depicted in FIG. 3 after being deconvoluted with the waves recorded in the basement.

The waveforms deconvolved with the signal recorded in the basement are graphically represented in FIG. 4 for each floor. The deconvolved wave in the basement is a single spike because a signal deconvolved with itself is a delta function. The deconvolved waves at all the floors are causal, i.e. they vanish for t<0. The first onset of the deconvolved waves is a wave that propagates upward in the building. A reflection of this wave by the top of the building is visible as the second peak in the waves that propagates downward in the building. The early part of the deconvolved waves consist of a superposition of upward and downward propagating waves. Since these waves interfere, it is difficult to identify the individual upward and downward propagating waves. The later part of the deconvolved waves consists of the resonance of the building. This resonance grows in amplitude with the floor level, and is fairly monochromatic.

Figure 5:
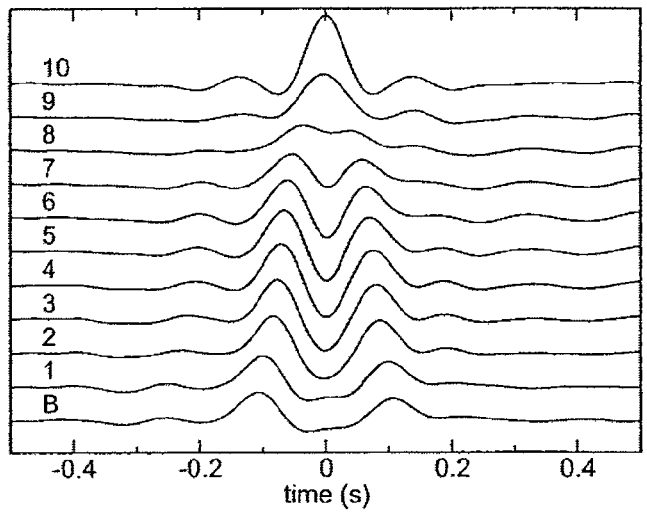
FIG. 5 is a graphical representation of the waveforms depicted in FIG. 3 after being deconvoluted with the waves recorded at the top floor.

The waveforms deconvolved with the signal recorded in the basement are fairly complex. In contrast, the waveforms deconvolved with the signal recorded at the top floor are much simpler, as shown in FIG. 5, which is a graphical representation of the waveforms for each floor deconvolved with the signal recorded at the top floor. These deconvolved waves are acausal and consist of the superposition of one upgoing wave and one downgoing wave. There is little indication that these upgoing and downgoing waves are reflected within the building. The reflection coefficients by the floors within the building therefore must be small. The reflection coefficient for elastic waves by a floor in the building depends on the product of the frequency and the mass of the floor. This means that the absence of waves reflected off the floors in the building may be due to the relatively low frequencies in the waveforms used in this study. In addition, the dominant wavelength of the employed waves spans several floors, this further suppresses reflections generated by the individual floors because a medium with small-scale variations can be treated as an effective medium that behaves like a homogeneous medium with properties that are determined by the background velocity and the embedded scatterers.

Figure 6:
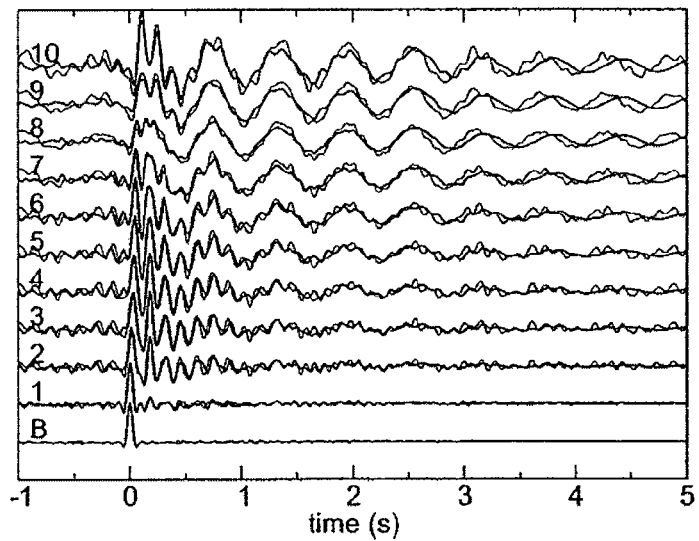
FIG. 6 is a graphical representation of the waveforms depicted in FIG. 3 at the different floors after being deconvoluted with the waves recorded in the basement. The deconvolved waves obtained using data in interval 1 are represented by the thick lines, while the deconvolved waves obtained using data in interval 2 are represented by the thin lines.

The deconvolved waveforms in the FIGS. 4 and 5 are computed from the full waveforms shown in FIG. 3. It is, however, not necessary to use the full waveforms. We have also deconvolved the signals using the time intervals 1 and 2 as shown in FIG. 3. Interval 1 straddles the S-wave arrival and is 4 s long, while interval 2 contains the surface wave arrivals and has a duration of 25 s. Both intervals were padded with zeroes to a duration of 40 s. The signals deconvolved with the waves recorded in the basement for each of the intervals are shown in FIG. 6. The thick line denotes the deconvolved waveforms from interval 1, while the thin line denotes the deconvolved waves from interval 2.

The similarity of the waves deconvolved over different time intervals is striking. Note how the deconvolved waves from interval 1 display the resonance of the building, despite the fact that these waves are based on the impulsive S-wave arrival only. The broadband nature of the S-wave ensures that sufficient low-frequency information is present to reproduce the resonance. Note also that the deconvolved waves from interval 2 are based on the surface wave signal. Nevertheless, these deconvolved waves display the upward and downward propagating waves early in the deconvolved signal. The recorded waves in interval 2 are dominated by low-frequency surface waves. These waves visually mask the higher frequency components in interval 2. The deconvolution equalizes the frequency content and therefore brings out the high-frequency propagating waves in FIG. 6. Interval 1 is shorter than interval 2, and one might think that interval 1 therefore contains less information than interval 2. Because of the impulsive character of the S-wave, the waves in interval 1 have a larger bandwidth than the waves in interval 2. This larger bandwidth helps stabilize the deconvolution. The similarity of the deconvolved waves for the intervals 1 and 2 shown in the FIGS. 6 and 7 implies that, for the level of shaking used in this study, the building responds linearly.

Figure 7:
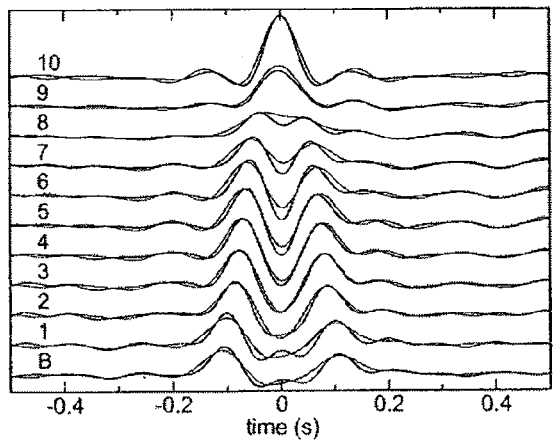
FIG. 7 is a graphical representation of the waveforms depicted in FIG. 3 at the different floors after being deconvoluted with the waves recorded at the top floor. The deconvolved waves obtained using data in interval 1 are represented by the thick lines, while the deconvolved waves obtained using data in interval 2 are represented by the thin lines.

The waves deconvolved with the signal recorded at the top floor for interval 1 and interval 2 is shown in FIG. 7 with a thick and thin line, respectively. As in the preceding figure, these deconvolved waves are similar. This implies that the S-wave and the surface wave both contain information about the upward and downward propagating waves in the building. The deconvolution defined in Expression 2 and the choice of are not optimized. A more careful choice of the deconvolution algorithm could make the deconvolved waves from the intervals 1 and 2 even more similar.

The deconvolved waves behave in the same way as a hologram. A part of a hologram can be used to reconstruct the image, albeit with a degraded resolution compared to the image of the full hologram. As shown in the FIGS. 6 and 7, the deconvolved waves that are computed from different sub-intervals of the whole signal lead to the same deconvolved waves.

IV. A Simple Model for the Wave Propagation in the Building.

In this Section we present a simple model for the wave propagation for the building. This simple model is for illustrative purposes only and should not be used to limit the subject invention, which is readily applicable to more complicated structures.

The base of the building is exposed to an external motion $s(t)$ with Fourier transform $S(\omega)$. In this model, the wave propagates upward in the building with a velocity c that is the shear velocity of the building. At the top of the building with height H the waves are reflected with reflection coefficient +1. During the upward and downward propagation, the waves attenuate; for a wave that travels over a distance L this is described by an attenuation operator $A(L,t)$. For a constant Q-model, this attenuation operator is in the frequency domain given by Expression 3, which is:

$$A(L,\omega) = \exp(-\gamma|\omega|L/c),$$

where $\gamma$ is related to the quality factor by Expression 4, which is:

$$\gamma = \tfrac{1}{2}Q.$$

The downward propagating waves reflect off the base of the building with a reflection coefficient $R(\omega)$ that corresponds in the time domain to a reflection operator $r(t)$. A wave $S(t)$ that travels upward in the building is given by $S(t-z/c)$. When the wave reflects off the top of the building, with reflection coefficient +1, the downgoing wave is given by $S(t-(2H-z)/c)$. When this downgoing wave reflects off the base of the building, it is deconvolved with the reflection operator $r(t)$. The wave that then travels upward is given by $r(t)*S(t-(2H+z)/c)$. The delay time $2H/c$ accounts for the time needed to propagate once up and down the building. This process can be continued for all the upward and downward propagating waves and is similar to the treatment of water-layer reverberations of M. M. Backus, Water reveberations—their nature and elimination, *Geophysics*, 24:233-261, 1959. After a convolution with the attenuation operators for each upward and downward going wave, the total response of the building is in the time domain given by Expression 5, which is:

$$u(z,t) = A(z,t)*s\left(t-\frac{z}{c}\right) + A(2H-z,t)*s\left(t-\frac{2H-z}{c}\right) +$$
$$r(t)*A(2H+z,t)*s\left(t-\frac{2H+z}{c}\right) +$$
$$r(t)*A(4H-z,t)*s\left(t-\frac{4H-z}{c}\right)$$
$$+\ldots$$

With the wave number defined by Expression 6, which is:

$$k = \omega/c,$$

and for the attenuation model of Expression 3, this expression is in the frequency domain given by Expression 7, which is:

$$u(z,\omega) = \sum_{n=0}^{\infty} S(\omega) R^n(\omega) \left\{ \begin{array}{l} e^{ik(2nH+z)} e^{-\gamma|k|(2nH+z)} + \\ e^{ik(2(n+1)H-z)} e^{-\gamma|k|(2(n+1)H-z)} \end{array} \right\}.$$

In this expression n counts the number of bounces off the base of the building. The first term denotes the upward propagating waves, while the last term accounts for the downward propagating waves that have bounced n times in the building.

The motion at height z deconvolved with the motion at the top floor is denoted by $T(z,\omega)$, so that in the frequency domain is given by Expression 8, which is:

$$T(z,\omega) \equiv \frac{u(z,\omega)}{u(z=H,\omega)}.$$

Similarly, the motion deconvolved with the motion at the bottom floor is denoted by $B(z,\omega)$. Thus, as given by Expression 9, which is:

$$B(z, \omega) \equiv \frac{u(z, \omega)}{u(z=0, \omega)}.$$

Let us first analyze T(ω). Inserting Expression 7 in the numerator and denominator of Expression 8 gives Expression 10, which is:

$$T(z, \omega) = \frac{\sum_{n=0}^{\infty} S(\omega) R^n(\omega) \left\{ \begin{array}{l} e^{ik(2nH+z)} e^{-\gamma|k|(2nH+z)} + \\ e^{ik(2(n+1)H-z)} e^{-\gamma|k|(2(n+1)H-z)} \end{array} \right\}}{2 \sum_{n=0}^{\infty} S(\omega) R^n(\omega) e^{ik2(n+1)H} e^{-\gamma|k|2(n+1)H}}.$$

Expression 10 can also be written as Expression 11, which is:

$$T(z, \omega) = \frac{\left\{ \begin{array}{l} e^{ik(z-H)} e^{-\gamma|k|(z-H)} + \\ e^{ik(H-z)} e^{-\gamma|k|(H-z)} \end{array} \right\} \sum_{n=0}^{\infty} S(\omega) R^n(\omega) e^{ik2(n+1)H} e^{-\gamma|k|2(n+1)H}}{2 \sum_{n=0}^{\infty} S(\omega) R^n(\omega) e^{ik2(n+1)H} e^{-\gamma|k|2(n+1)H}}.$$

The excitation S(ω) and the sum with the reverberations in the numerator and the denominator cancel, resulting in Expression 12, which is:

$$T(z, \omega) = \frac{1}{2} \{ e^{ik(z-H)} e^{-\gamma|k|z-H|} + e^{ik(H-z)} e^{-\gamma|k|(H-z)} \}.$$

This means that T(z,ω) accounts for the sum of one attenuating upgoing wave and one downgoing wave. Since z<H, the upgoing wave is acausal. The cancellation of the sum over reverberations means that T(z,ω) is independent of the reverberations in the building. The cancellation of the reflection coefficient R(ω) implies that T(z,ω) does not depend on the coupling of the building to the subsurface. The cancellation of S(ω) means that the deconvolved response is independent of the excitation of the building.

A similar analysis can be applied to the building response deconvolved with the motion at the base. Inserting Expression 7 in the numerator and denominator of Expression 9 gives Expression 13, which is:

$$B(z, \omega) = \frac{\sum_{n=0}^{\infty} S(\omega) R^n(\omega) \left\{ \begin{array}{l} e^{ik(2nH+z)} e^{-\gamma|k|(2nH+z)} + \\ e^{ik(2(n+1)H-z)} e^{-\gamma|k|(2(n+1)H-z)} \end{array} \right\}}{\sum_{n=0}^{\infty} S(\omega) R^n(\omega) \{ e^{ik2nH} e^{-\gamma|k|2nH} + e^{ik2(n+1)H} e^{-\gamma|k|2(n+1)H} \}}.$$

Factoring out the summations, Expression 13 can be written as Expression 14, which is:

$$B(z, \omega) = \frac{\left\{ \begin{array}{l} e^{ikz} e^{-\gamma|k|z} + \\ e^{ik(2H-z)} e^{-\gamma|k|(2H-z)} \end{array} \right\} \sum_{n=0}^{\infty} S(\omega) R^n(\omega) e^{ik2nH} e^{-\gamma|k|2nH}}{\{1 + e^{2ikH} e^{-2\gamma|k|H}\} \sum_{n=0}^{\infty} S(\omega) R^n(\omega) e^{ik2nH} e^{-\gamma|k|2nH}}.$$

The summation over the reverberations, the reflection coefficient R(ω), and the excitation S(ω) cancel, resulting in Expression 15, which is:

$$B(z, \omega) = \frac{e^{ikz} e^{-\gamma|k|z} + e^{ik(2H-z)} e^{-\gamma|k|(2H-z)}}{1 + e^{2ikH} e^{-2\gamma|k|H}}.$$

Just as for the signals deconvolved with the top floor, this deconvolved signal depends neither on the coupling with the ground nor on the excitation.

The deconvolved response T(z,ω) is the superposition of one acausal upgoing wave and one causal downgoing wave. Such a simple interpretation cannot be applied to B(z,ω) because the numerator depends on frequency. The deconvolved response can be interpreted in two ways: as a superposition of traveling waves; or as a superposition of modes. The traveling wave interpretation is obtained by using the following geometric series in Expression 16, which is:

$$\frac{1}{1 + e^{2ikH} e^{-2\gamma|k|H}} = \sum_{n=0}^{\infty} (-1)^n e^{2iknH} e^{-2\gamma|k|nH}.$$

Because of the attenuation this sum is guaranteed to converge. Inserting this in Expression 11 gives B(z,ω) as an infinite sum of upgoing and downgoing traveling waves, as provided in Expression 17, which is:

$$B(z, \omega) = \sum_{n=0}^{\infty} (-1)^n \{ e^{ik(z+2nH)} e^{-\gamma|k|(z+2nH)} + e^{ik(2(n+1)H-z)} e^{-\gamma|k|(2(n+1)H-z)} \}.$$

The difference with Expression 15 is that the frequency-dependent denominator has disappeared. Note that since the argument of each of the complex exponentials is positive, B(z,ω) is a causal function. This deconvolved response is an infinite sum of upgoing and downgoing attenuated waves. This sum differs from the sum of upgoing and downgoing waves in the building, because B(z,ω) does not depend on the ground coupling, whereas the original sum of upgoing and downgoing waves of Expression 7 does depend on the ground coupling through the reflection coefficient R(ω).

In Expression 17, the reflection coefficient at the base of the building is equal to −1, because the wave that has bounced n times off the base of the building is proportional to $(-1)^n$. There is a simple explanation for this. The deconvolution of the motion of the basement with itself gives, by definition, a bandpass-filtered delta function as shown in the bottom trace of FIG. 4. When the wave that has reflected off the top of the building propagates downward, it must give a vanishing contribution at the base of the building because the deconvolved wave at that level vanishes for t>0. The motion at the base can only vanish when an upward propagating wave is launched upward with the opposite polarity as the downward propagating wave that strikes the basement. This corresponds to a reflection coefficient for the deconvolved waves that is equal to −1 rather than the reflection coefficient R(ω) of the subsurface. It has been shown earlier that seismic interferometry can be used to determine waveforms for the system with different boundary conditions than the physical boundary conditions. D. C. Riley and J. F. Claerbout, 2-D multiple reflections, *Geophysics*, 41:592-620, 1976; K. Wapenaar, J. Thorbecke, and D. Dragonov, Relations between reflection and transmission responses of three-dimensional inhomogeneous media, *Geophys. J. Int.*, 156:179-194, 2004. Riley and Claerbout coined the phrase Noah's deconvolution for this technique.

An alternative way to interpret $B(z,\omega)$ is based on normal modes. Using the inverse Fourier transform, and Expression 6, the deconvolved response is in the time domain given by Expression 18, which is:

$$B(z,t) = \int_{-\infty}^{\infty} \frac{e^{-i\omega(t-z/c)}e^{-\gamma|\omega|z/c} + e^{-i\omega(t-(2H-z)/c)}e^{-\gamma|\omega|(2H-z)/c}}{1+e^{2i\omega H/c}e^{-2\gamma|\omega|H}} d\omega.$$

As shown in Section VII, this integral can be solved by contour integration. The integrand has simple poles, as shown in Expression 19, which is:

$$1+e^{2i\omega H/c}e^{-2\gamma|\omega|H}=0,$$

Figure 8:
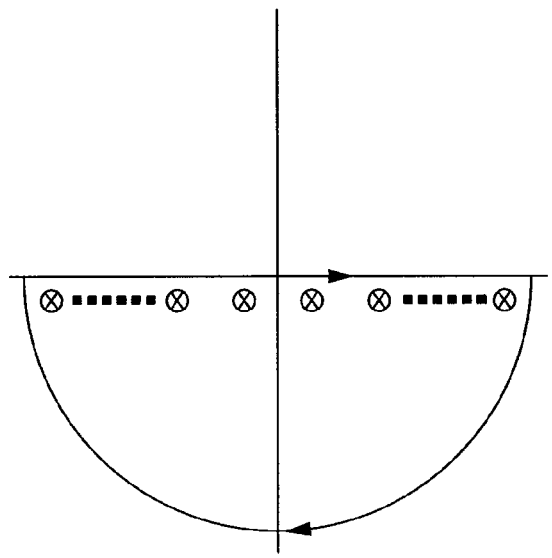
FIG. 8 is a graphical representation of the location of the poles in the complex $\omega$-plane and the contour integration that is used for $t>(2H-z)/c$.

The location of the poles in the lower half-plane is shown in FIG. 8. For $t>(2H-z)/c$, the contour must be closed in the lower half plane, and as shown in Section VII, the integral of Expression 18 can be written as a sum of damped normal modes, as shown in Expression 20, which is:

$$B(z,t) = \frac{4\pi c}{H}\sum_{m=0}^{\infty}(-1)^{m+1}\exp(-\gamma\omega_m t)\cos\left(\frac{\omega_m(H-z)}{c}\right)\sin(\omega_m t),$$

wherein $\omega_m$ is as shown in Expression 21, which is:

$$\omega_m = \frac{(m+1/2)\pi c}{H}$$
$$m = 0,1,2,\ldots$$

It should be noted that these normal modes are not the normal modes of the building, because its normal modes depend in general on the coupling to the ground. The normal modes in the sum (i.e., Expression 20) are independent of the reflection coefficient $R(\omega)$, hence the normal modes in the deconvolved response depend on the properties of the building only. This is consistent with the traveling wave formulation of Expression 17, where the reflection coefficient for the deconvolved wave is equal to $-1$ rather than the reflection coefficient $R(\omega)$ of the subsurface.

Each term in the sum (i.e., Expression 20) is exponentially damping. The term with the fundamental mode (m=0) has the smallest damping. This means that for large times ($t \gg 2H/\pi c$) the fundamental mode dominates as shown in Expression 22, which is:

$$B(z,t) \approx \frac{4\pi c}{H}\exp(-\gamma\omega_0 t)\cos\left(\frac{\omega_0(H-z)}{c}\right)\sin(\omega_0 t),$$

wherein $\omega_0$ is as shown in Expression 23, which is:

$$\omega_0 = \frac{\pi c}{2H}.$$

The period that corresponds to this angular frequency is given by Expression 24, which is:

$$T_0 = \frac{4H}{c}.$$

Note that this is the time needed to propagate up and down the building twice. This period is determined by the factor $(-1)^m$ in Expression 17. Because of this factor the wave changes polarity if it propagates up and down the building once. If the wave travels up and down the building twice and covers a distance 4H, the polarity changes twice and the reverberating wave reinforces itself to form a resonance.

V. Interpretation of The Deconvolved Waveforms.

The theory of Section IV agrees with the deconvolved waves in FIGS. 4 and 5. Let us first consider the waves deconvolved with the waves at the top floor as shown in FIG. 5. These deconvolved waves are given by Expression 12 that gives the superposition of an acausal upgoing wave and a causal downgoing wave; both waves are clearly visible in FIG. 5. Given the floor spacing of 4.27 m, these waves can be used to estimate the shear velocity in the building. It follows from Expression 12 that if there is no attenuation ($\gamma=0$), and if the data have infinite bandwidth, that the deconvolution is in the time domain given by a superposition of upward and downward propagating delta functions, as illustrated in Expression 25, which is:

$$T(z,t) = \pi\left\{\delta\left(t - \frac{z-H}{c}\right) + \delta\left(t + \frac{z-H}{c}\right)\right\}.$$

In deriving this result, Expression 6 is used. The attenuation and the finite bandwidth of the data cause the broader pulses shown in FIG. 5.

Figure 9:
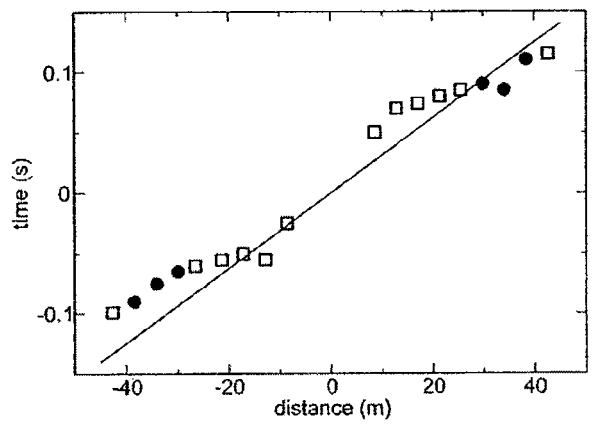
FIG. 9 is a graphical representation of the upgoing and downgoing waves in FIG. 5. A negative distance/time corresponds to the upgoing wave, a positive distance/time to the downgoing wave. The travel times at the floors 1-3 are marked with solid circles. The solid line indicates the travel time predicted for the shear velocity inferred from the normal mode measurements that give a velocity of 322 m/s.

We measured the arrival time of the upward and downward propagating waves by picking the maximum of these waves. These arrival times are shown in FIG. 9. The distance is measured relative to the position of the accelerometer at the top floor. For the upward propagating wave, this distance is given a negative value. For the floors 4-10, the upward and downward propagating waves overlap. This may bias the travel time measurements. The travel times at these floors are indicated with open squares. The travel time determined from the waves recorded in the basement may be biased by the presence of the solid earth below the basement. These travel times are also indicated with open squares. Despite these reservations, the measurements in FIG. 9 display a fairly linear dependence of the travel time with distance. This indicates a constant shear velocity in the building.

Figure 10:
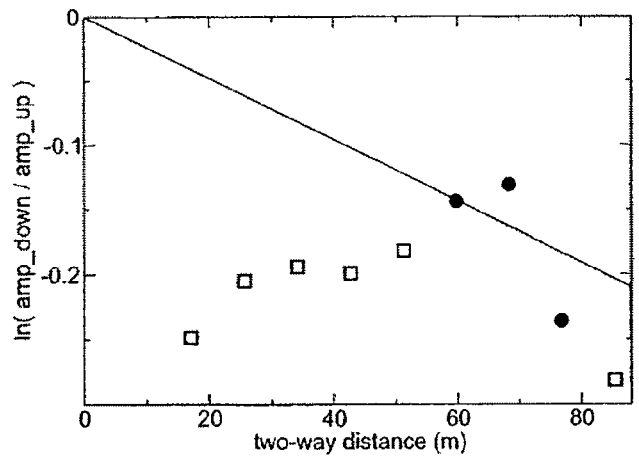
FIG. 10 is a graphical representation of the nature logarithm of the ratio of the amplitudes of the upgoing and downgoing waves of FIG. 5 as a function of the two-way distance to the top of the building. The amplitude ratio for floors 1-3 is indicated with solid circles. The log-amplitude ratio predicted by the attenuation of Q=20.45 is shown with the straight line.

According to Expression 12, the upward and downward propagating waves both decay due to attenuation. This attenuation can be seen in FIG. 5 because the downward going wave has a consistently smaller amplitude than the upward propagating wave. The absolute value of the amplitude at different floors cannot be compared with great accuracy, because the absolute amplitude is effected by the receiver coupling and other uncertainties. The ratio of the amplitude of the downgoing wave and the upgoing wave, however, does not depend on the receiver coupling. FIG. 10 shows the natural logarithm of the ratio of the downgoing wave and the upgoing wave at each floor. The amplitude measurements in the floors 4-10 and in the basement are likely to be unreliable because of the interference of the upgoing and downgoing waves and the presence of the solid earth below the basement, respectively. The amplitude ratios at these levels are indicated with open squares. The amplitude ratio for the floors 1-3 is indicated by solid circles and are most reliable. The two-way distance is measured relative to the receiver at the top floor. The scatter in the amplitude ratio is considerable because the amplitude difference between the upgoing and downgoing waves is fairly small. In a taller building, these amplitude differences would be larger, and the attenuation can be determined with greater accuracy.

According to Expressions 17 and 20, the signals deconvolved with the bottom floor can be seen either as a superposition of upward and downward propagating waves, or as a sum of normal modes. The interpretation in terms of propagating waves is most useful for the early part of the deconvolved waves in FIG. 4. In that figure, the upward and downward propagating waves are not as clear as in FIG. 5 for the waves deconvolved with the signals at the top floor, because in FIG. 5 only one upgoing wave and one downgoing wave are present, whereas according to Expression 17 many upgoing and downgoing waves interfere with each other in FIG. 4. For this reason we analyze the waves deconvolved with the signal in the basement in FIG. 4 from the normal mode point of view as formulated in Expression 20. Since the fundamental mode is much stronger than the higher modes, we use the Expressions 22 through 24 in the following.

The amplitude spectrum of the deconvolved waves of FIG. 4 averaged over all the floors has a pronounced peak at 1.72 Hz. This reflects the monochromatic nature of the resonance. Given that the height of the building measured to the basement is 47 m, this gives with Expression 24 a shear velocity of:

$$c=322 \text{ m/s}$$

The travel time as a function of distance for this velocity is indicated by the solid line in FIG. 9. The proximity of this travel time curve to the arrival times of the upward and downward propagating waves shows that the traveling waves and the normal modes predict a shear velocity that is similar. This provides a consistency check on the analysis. A systematic difference between the velocity of the propagating waves and the normal modes can be due to dispersion caused by the internal structure in the building, and to amplitude variations between floors that are ignored in Expression 4 that forms the basis of the mathematical model of Section IV.

Figure 11:
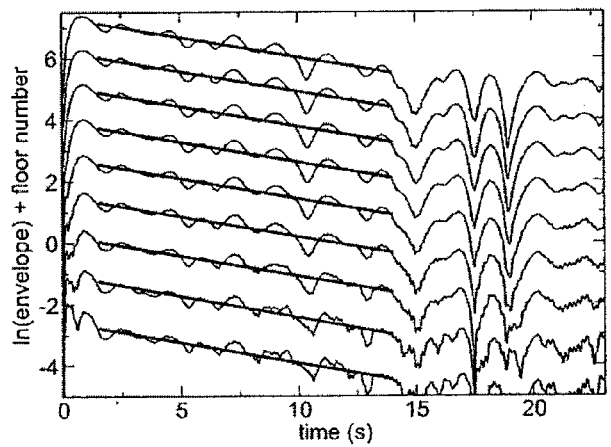
FIG. 11 is a graphical representation of the natural logarithm of the envelope of the deconvolved waves in FIG. 4 after applying a bandpass filter with corner frequencies of 1 Hz to 3 Hz, respectively. For clarity, the floor number is added to each curve. The best-fitting straight line to each curve is indicated with thick solid lines.

According to Expression 22 the resonance decays with time due to an elastic attenuation. In order to quantify the attenuation, we bandpass filtered the deconvolved waves of FIG. 4 with a Butterworth filter with cutoff frequencies of 1 and 3 Hz, respectively. This filter extracts the fundamental mode from the waveforms. The natural logarithm of the envelope of the bandpass-filtered waveforms is shown in FIG. 11. Since the resonance is weak for the lowest floor, we used only the top 9 floors in the normal-mode analysis. We added the floor number to each curve in order to separate them in the figure. Since only the slope depends on the attenuation, this offset does not affect the analysis. Note that, apart from some fluctuations, the envelope of the deconvolved waves decays with time. This contrasts the original waveforms in FIG. 3 that do not decay with time because the motion is continuously excited by the surface waves. The deconvolution extracts the decay of the resonance with time, this makes it possible to measure the an elastic attenuation in the building.

Between 1.5 s and 14 s the logarithm of the envelope decays linearly with time. This is consistent with the exponential decay in Expression 22. For later times the resonance is of the same order of magnitude as the ambient noise, and the exponential decay is not valid. In order to determine the attenuation we fitted straight lines to the curves for 1.5 s<t<14 s. The least-squares fit of the envelopes is shown by the solid lines in FIG. 11. The slopes are similar and the average slope is given by Expression 26, which is:

$$\text{slope}=-0.1321\pm 0.0017 \text{ s}^{-1}.$$

The error is determined by the standard deviation of the slope for the deconvolved waves at different floors. According to the Expressions 4 and 22, the slope is equal to $-\omega/2Q$. For the resonant frequency of 1.72 Hz, this gives:

$$Q=20.45.$$

This value of the attenuation can be compared with the attenuation of the propagating waves shown in FIG. 10. The propagating waves in FIG. 5 have a dominant frequency of about f=5 Hz. The propagating waves decay with distance as $\exp(-\pi f z/Qc)$. For the value of Q given above, and a velocity of 322 m/s, this decay is shown by the solid line in FIG. 10. The variability in the amplitude measurements in that figure is fairly large. For the lower three floors where the upgoing and downgoing waves don't interfere, the attenuation inferred from the resonance agrees with amplitude decay determined from the propagating waves as indicated with the solid circles. The comparison of the attenuation from the normal modes and the propagating waves provides a consistency check on the employed model of wave propagation in the building.

VI. Discussion.

We have shown that the deconvolution of the motion recorded at different floors in the building is an effective tool for extracting the building response. The deconvolution with respect to the signals recorded in the basement and the top floor provide complementary information. The deconvolution with the signal recorded at the top floor gives one upgoing and one downgoing propagating wave that clearly are separated. The deconvolution with the waveforms recorded in the basement provides information on the fundamental mode of the building.

The deconvolved waves are independent of the excitation and of the ground coupling. This can be seen in Expressions 12 and 15 that are independent of the excitation $S(\omega)$ and the reflection coefficient $R(\omega)$ at the base of the building. Suppose that instead of the deconvolution, we had used the correlation, as is common in seismic interferometry. In the frequency domain, the correlation of the waves recorded at height z with those in the basement is given by Expression 27, which is:

$$C(z,\omega)=u(z,\omega)u^*(z=0,\omega).$$

When Expression 7 is inserted in this expression, the result contains the power spectrum $|S(\omega)|^2$ of the excitation as well as products of the reflection coefficient $R(\omega)$. In contrast to this, the deconvolved waves of Expressions 12 and 15 depend on neither of these quantities.

Figure 12:
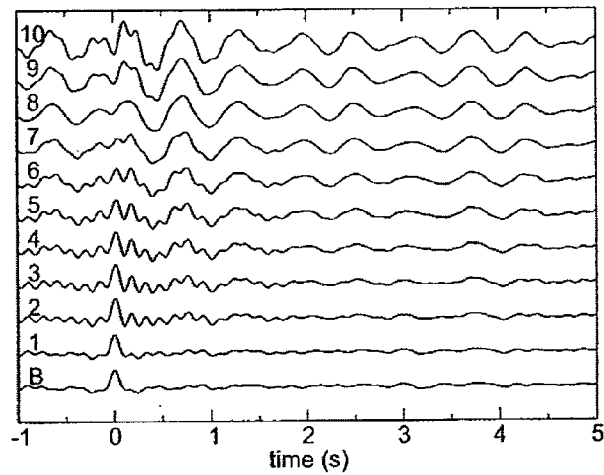
FIG. 12 is a graphical representation of the waveforms of FIG. 3 at the different floors after correlation with the waves recorded in the basement.

It is instructive to consider the waveforms obtained from correlation with the signal in the basement as defined by Expression 27. These correlated waveforms are shown in FIG. 12. This figure should be compared with FIG. 4 for the deconvolved waves. The deconvolved waves are causal while the waveforms obtained by correlation are not. This is due to the fact that the waveforms computed by correlation depends on the power spectrum $|S(\omega)|^2$ of the excitation. The multiplication with the power spectrum in the frequency domain corresponds in the time domain to a convolution with the autocorrelation of the excitation. For the surface waves that excite the building, this autocorrelation has a fairly long time duration. This leads to a-casual arrivals in the correlated waves of FIG. 12. Note that the waveforms computed from correlation show neither the upgoing and downgoing waves nor the clear resonance of the deconvolved waves of FIG. 4. This means that for this application deconvolution is superior to correlation.

Expression 12 can be generalized for SH-waves in an arbitrary layered medium. In this case the deconvolved waves $T(z,\omega)$ are equal to the $P_{11}$-element of the propagator matrix. J. Trampert, M. Cara, and M. Frogneux, Shear propagator matrix and qs estimates from borehole- and surface-recorded earthquake data, *Geophys. J. Int.*, 112:290-299, 1993. This contrasts formulations of seismic interferometry based on correlation where the Green's function is obtained. O. I. Lobkis and R. L. Weaver, On the emergence of the Green's function in the correlations of a diffuse field, *J. Acoust. Soc. Am.*, 110:3011-3017, 2001; A. Derode, E. Larose, M. Campillo, and M. Fink, How to estimate the Green's function for a heterogeneous medium between two passive sensors?Application to acoustic waves, *Appl. Phys. Lett.*, 83:3054-3056, 2003; R. Snieder, Extracting the Green's function for the correlation of coda waves: a derivation bases on stationary phase. *Phys. Rev. E.*, 69:046610, 2004; K. Wapenaar, Retrieving the elastodynamic Green's function of an arbitrary inhomogeneous medium by cross correlation, *Phys. Rev. Lett.*, 93:254301, 2004; R. Snieder, Spourious multiples in interferometric imaging of primaries, *Geophysics*, submitted 2005. According to expression (7.43) of K. Aki and P. G. Richards, Quantitative Seismology, *Univ. Science Books*, Sausalito, second edition, 2002, the $P_{11}$-element of the propagator matrix for SH-waves in a lossless homogeneous medium is given by Expression 28, which is:

$$P_{11}(z, H) = \cos k(z - H) = \frac{1}{2}(e^{ik(z-H)} + e^{ik(H-z)}).$$

Apart from terms that depend on the attenuation this expression is identical to Expression 12. It can be shown that this is also the case for a general layered medium that has internal reflections.

The deconvolved waves can be used to estimate the shear velocity and attenuation in the Millikan Library. The waves deconvolved with the motion in the top floor lead to clear upgoing and downgoing waves. The velocity of propagation can be measured from the arrival time of these waves, while the ratio of the amplitude of the upgoing and downgoing waves constrains the attenuation. The waveforms obtained by deconvolution with the motion in the basement gives the motion of the fundamental mode of the building. The frequency and temporal decay constrain the shear velocity and attenuation as well. As shown in FIGS. 9 and 10, these complementary pieces of information are consistent. This shows that the deconvolution of the motion in the building recorded at different levels can successfully be used to eliminate the imprint of the excitation and the ground coupling, and that the values of the shear velocity and attenuation from propagating waves and from the fundamental mode are consistent.

VII. Evaluation of the Fourier Integral.

In this Section, we evaluate the Fourier integral 18 using complex integration. For $t>(2H-z)/c$ the integration along the real $\omega$-axis must be closed in the lower half plane to obtain a vanishing contribution of the semi-circular integration path that is added in the contour integration. R. Snieder, *A Guided Toure of Mathematical Methods for the Physical Sciences*, Cambridge Univ. Press, Cambridge, UK, 2nd edition, 2004. The value of the contour integral over the path shown in FIG. 8 is determined by the poles of the integrand in Expression 18 in the lower half-plane. The pole-positions are determined by Expression 19. To first order in r, the poles are located per Expression 30, which is:

$$\omega_* = \mp \omega_m - i\gamma\omega_m \quad (m=0,1,2,\dots),$$

with $\omega_m$ given by Expression 21. There are infinitely many poles at locations in the lower half-plane as shown in FIG. 8.

The terms in the integrand in Expression 18 are of the form as indicated in Expression 31, which is:

$$I = \int_{-\infty}^{\infty} \frac{f(\omega)}{1 + e^{i\omega\tau}e^{-\gamma|\omega|\tau}} d\omega,$$

where $f(\omega)$ is an analytic function. Setting $\omega=\omega_*+\xi$ and using a first-order Taylor expansion in $\xi$ gives Expression 32, which is:

$$1 + e^{i\omega\tau}e^{-\gamma|\omega|\tau} = -i\xi\tau + O(\xi^2).$$

This implies that the poles are simple and that the residue for the pole at $\omega_*$ is given by Expression 33, which is:

$$Res \frac{f(\omega)}{1 + e^{i\omega\tau}} = \frac{f(\omega_*)}{-i\tau},$$

Together with the factor $-2\pi i$ from the counter-clockwise contour integration, this gives a contribution $2\pi f(\omega_*)/\tau$ to the complex integral. Using this in the integral in Expression 18 and taking the poles in the 3rd and 4th quadrant into account gives Expression 34, which is:

$$B(t) = \frac{2\pi c}{H} \sum_{m=0}^{\infty} e^{-\gamma\omega_m t} \{\cos(\omega_m(t - z/c)) + \cos(\omega_m(t - (2H - z)/c))\}.$$

Using trigonometric identities, the terms in curly brackets equals Expression 35, which is:

$$\cos(\omega_m(t - z/c)) + \cos(\omega_m(t - (2H - z)/c)) =$$
$$2\cos(\omega_m H/c)\cos(\omega_m(H - z)/c)\cos(\omega_m t) -$$
$$2\sin(\omega_m H/c)\cos(\omega_m(H - z)/c)\sin(\omega_m t).$$

According to Expression 21, $\cos(\omega_m H/c)=0$ and $\sin(\omega_m H/c)=(-1)^m$, so that Expression 36 is:

$$\cos(\omega_m(t-z/c))+\cos(\omega_m(t-(2H-z)/c))=2(-1)^{m+1} \cos(\omega_m(H-z)/c)\sin(\omega_m t).$$

Using this in Expression 34 gives Expression 20.

VIII. Retrieval of the Response of the Structure were the Structure to have Different Boundary Conditions FIG. 5 was obtained by deconvolving the motion at every floor with the motion recorded at the top floor. These deconvolved waves show one upgoing wave and one downgoing wave. This wave state is a-causal (meaning it is nonzero for $t<0$), and the downward propagating wave does not reflect off the base of the building. (It satisfies radiation boundary conditions.) This means that FIG. 5 represents a wave state of the building, as if the base of the building was not reflecting. This contrasts the real building, where wave are reflected off the base of the building.

In contrast, FIG. 6 shows the waves at all floors after deconvolution with the motion at the base of the building.

This corresponds to a wave state that has reflection coefficient R=−1 at the base of the building. This reflection coefficient, again, is different from the reflection coefficient at the real building.

These examples show that the proposed deconvolution method makes it possible to compute from the data new wave states of the building that satisfy different boundary conditions than the real building does. This can be used to highlight different structural properties of the building. For example, the wave velocity of the upgoing and downgoing waves can easily be extracted from the wave state in FIG. 5, whereas the attenuation of the resonance that dominates the wave state of FIG. 6 can be used to estimate the attenuation of the building. A comparison of the FIGS. 5 and 6 also shows that these different wave-states are sensitive to the building response at different frequencies.

Figure 13:
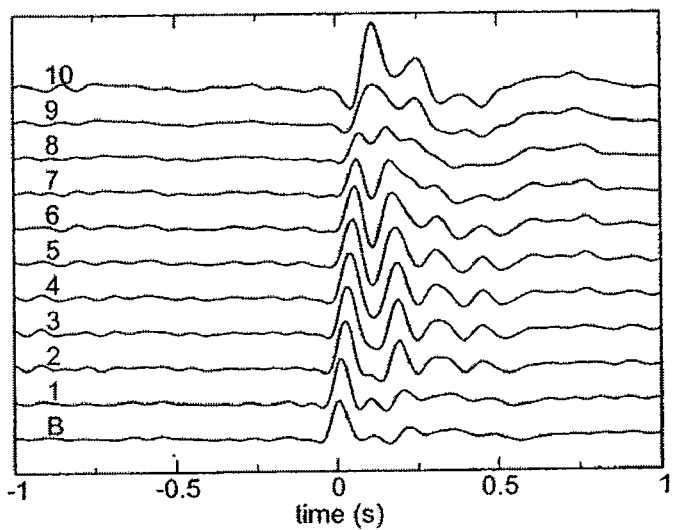
FIG. 13 is a graphical representation of the waveforms of FIG. 3 at every floor deconvolved with the upgoing wave in the basement.

The ability that one has with the method proposed here to create wave states of the building as if it was subject to different boundary conditions can be taken further. FIG. 13 shows the wavefield at every floor after deconvolution with the upgoing wave at the basement (z=0). For this wave state, the upgoing wave in the basement is collapsed by the deconvolution process to a band-limited delta function. This means that for t≠0 this wave state contains only downgoing waves at the basement. Indeed, the waves of FIG. 13 only show downgoing waves for t≠0. These downgoing waves are (by definition) not reflected off the base off the building, otherwise there would be upgoing waves as well. This means that the wave state of FIG. 13 satisfies radiation boundary condition at the base of the building. (In contrast to the real building.) The wave state of FIG. 13 is useful for practical purposes, because the internal reflections of waves by different floors in the building are more pronounced than in the wave states shown in the FIGS. 5 and 6.

Figure 14:
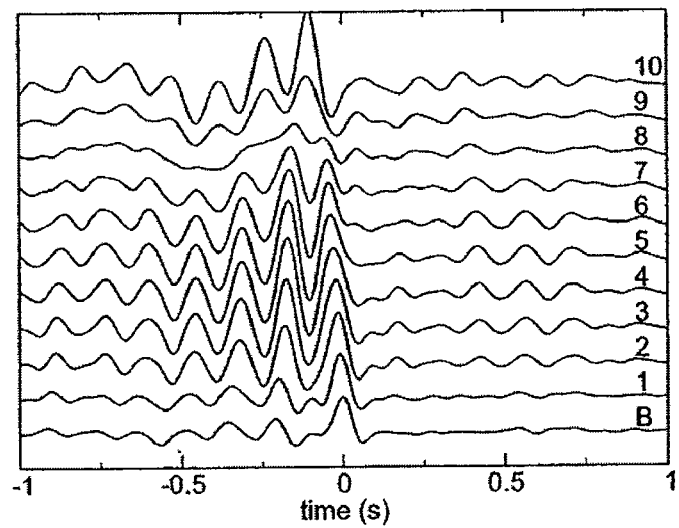
FIG. 14 is a graphical representation of the waveforms of FIG. 3 at every floor deconvolved with the downgoing wave in the basement.

It is, of course, also possible to deconvolve the waves recorded at every floor with the downgoing waves in the basement. The resulting wave state is shown in FIG. 14. In this wave state the downgoing wave in the basement is compressed to a band-limited delta function centered at t=0. This means that for t≠0 this wave state only has upgoing waves in the basement.

One might think that this wave state is the time-reversed version of FIG. 13. A comparison of the FIGS. 13 and 14 shows that this is not the case. This can be seen in FIG. 15 where the waveforms of FIG. 13 are superposed on the time-reversed version of the waveforms of FIG. 14. The invariance for time-reversal is broken by the attenuation in the building (Q≈20). The differences of the waveforms are thus due to the attenuation in the building. These differences can be used to estimate the attenuation in the building in yet another way.

Figure 15:
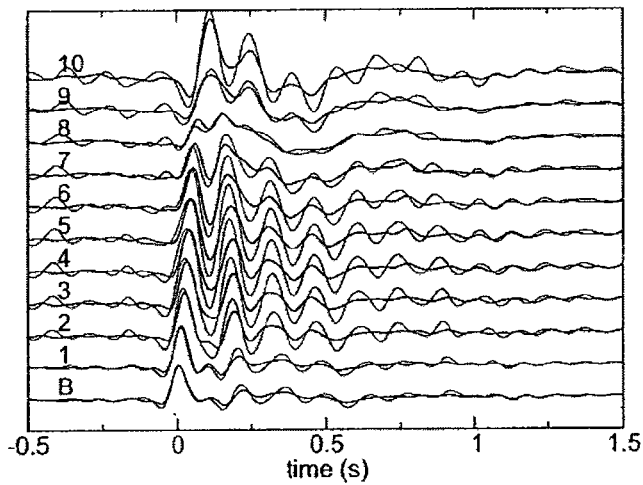
FIG. 15 is a graphical representation of the waveforms of FIG. 13 (thick lines) superposed over the time-reversed version of the waveforms of FIG. 14 (thin lines).
Figure 16:
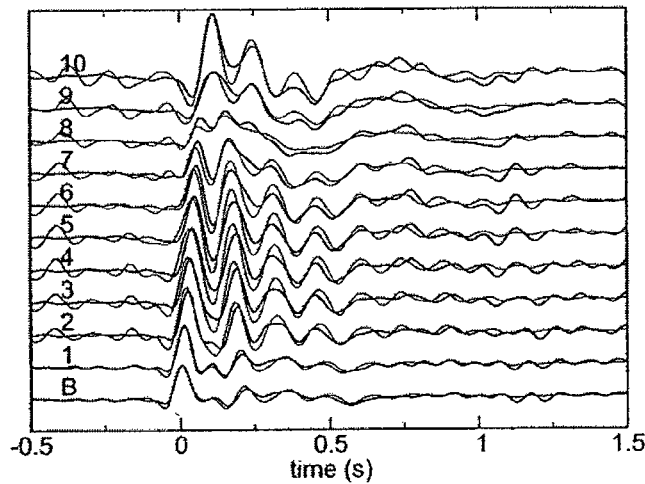
FIG. 16 is a graphical representation of the waveforms of FIG. 15 at every floor after multiplication with $\exp(-t/\tau)$ (thick lines) and $\exp(+t/\tau)$ (thin lines), respectively, using $\tau=1.4$ s.

FIG. 16 shows the waveforms of FIG. 15 after multiplication with a factor $\exp(-t/\tau)$ for the waveforms of FIG. 13 and after multiplication with a factor $\exp(+t/\tau)$ for the waveforms of FIG. 14. In FIG. 15 the value $\tau=1.4$ s is used. This is a crude way to account for the an-elastic attenuation in the building. One could, of course, convolve with more accurate representations of the attenuation operator. For a dominant frequency of 5 Hz, this value of $\tau$ corresponds to a quality factor Q=22. This value agrees well with the quality factor obtained from the normal-mode response in FIG. 11.

These examples show that by making different combinations of the waves recorded at different locations, one can create wave states in the building under a variety of different boundary conditions. This can be exploited to highlight certain different aspects of the dynamic response of the structure (e.g., different frequency bands, internal reflections, attenuation).

IX. A System and Method of Monitoring the Structural Integrity of a Structure.

As explained in more detail in the preceding Sections of this Detailed Description, the motion of a structure (e.g., a building) during a period of excitation is a function of the following components or effects: the excitation experienced by the structure; the coupling of the structure to its support base (e.g., the ground in the context of a building); and the structural response (i.e., the mechanical properties) of the structure. Two of the mechanical properties that are of interest include the rate at which shear waves propagate through the structure (i.e., the structure's shear velocity) and the structure's ability to attenuate the wave energy resulting from an excitation (i.e., the structure's attenuation).

By deconvolving the motion recorded at different locations within or on the structure (e.g., at different floor levels in the context of the building), it is possible to separate the structural response of the structure from the effects of the excitation and the base coupling. The structural response of the structure is dependent on the structure's mechanical properties and is independent of the excitation and base coupling. Thus, it is possible to monitor the structural integrity of a structure over a period of time by employing the methodology discussed in the preceding Sections.

The excitation experienced by the structure can result from a variety of natural or non-natural events. For example, natural events that can cause a structure to experience excitation include seismic occurrences resulting from earthquakes, volcanoes, landslides, avalanches, etc. Natural events that can cause a structure to experience excitation also include weather generated events such as winds from severe weather, tornados, hurricanes, etc. Non-natural events that can cause a structure to experience excitation include explosions (whether the result of accident, war, terrorism, demolition, mining, etc.). Non-natural events that can cause a structure to experience excitation also include impact forces (e.g., a body impacting the structure or near the structure).

Figure 17:
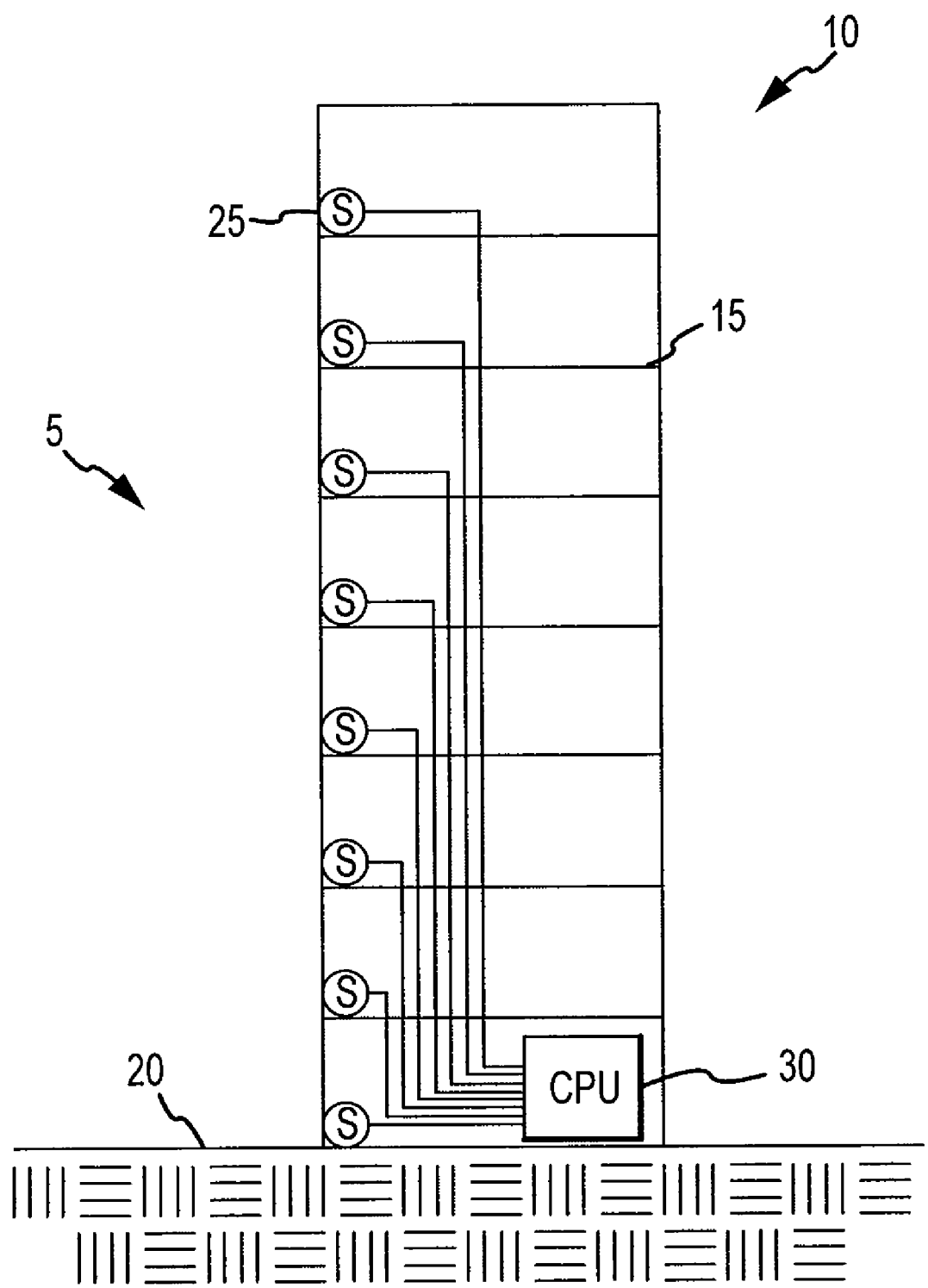
FIG. 17 is a diagrammatic representation of a system employing the method of the subject invention, wherein a generic structure has a structural framework coupled to a support base.
Figure 18:
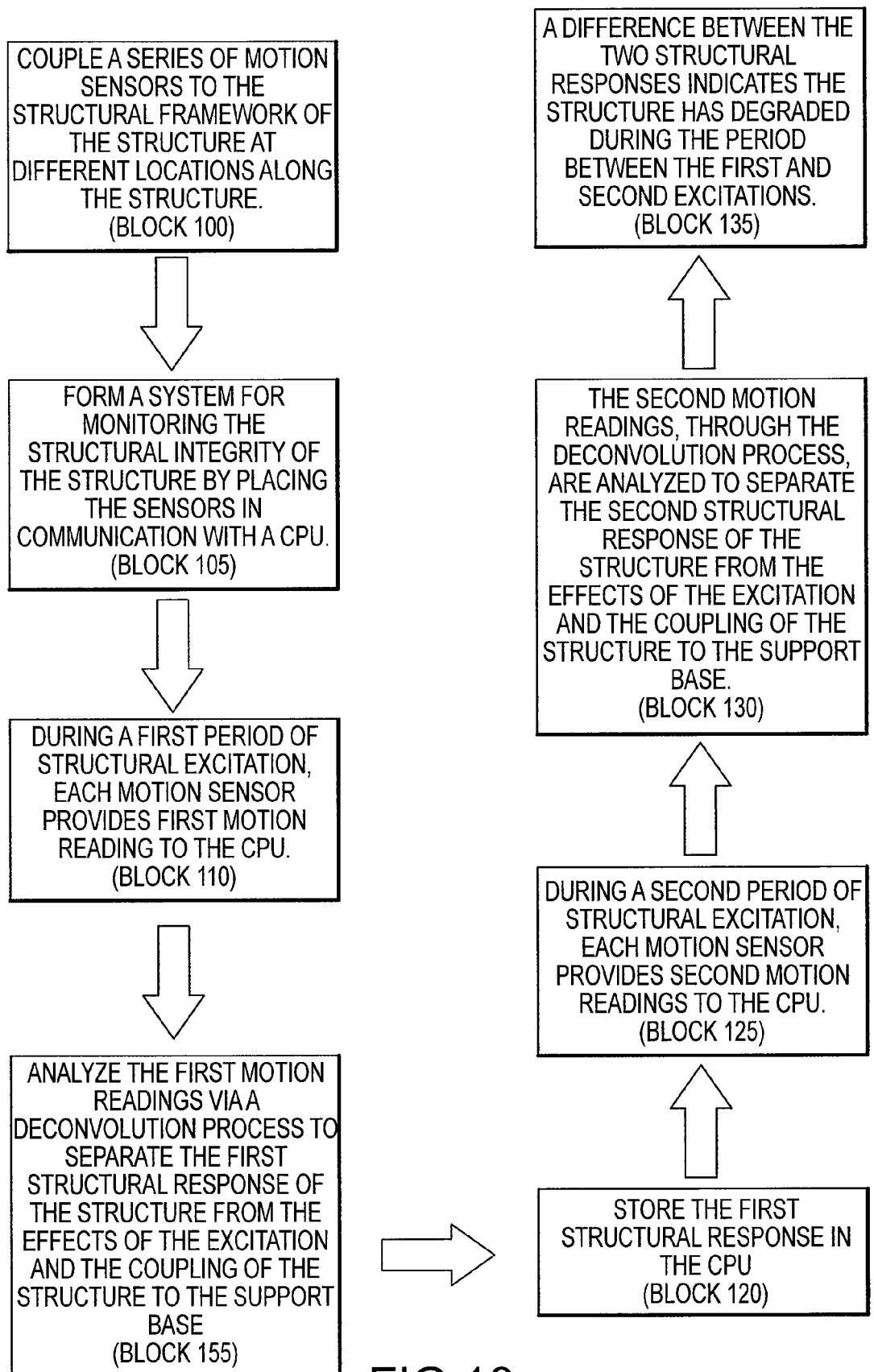
FIG. 18 is a block diagram outlining the method of the subject invention.

For a discussion of a system and method for monitoring the structural integrity of a structure 10, reference is now made to FIGS. 17 and 18. FIG. 17 is a diagrammatic representation of a system 5 employing the method of the subject invention, wherein a generic structure 10 has a structural framework 15 coupled to a support base 20. FIG. 18 is a block diagram outlining the method of the subject invention.

The method and system of the subject invention are readily applicable to a wide variety of applications where it would be beneficial to monitor the structural integrity of a structure. For example, in one application, the structure 10 depicted in FIG. 17 is a building and the support base 20 is the foundation and ground supporting the building. In another application where it is desired to monitor the structural integrity of a building portion (e.g., several of the building's upper floors or the roof structure of the building), the structure 10 is the building portion and the support base 20 is rest of the building supporting said building portion.

As can be easily understood, the method and system of the subject invention are readily applicable to other constructed structures. In other words, the method and system of the subject invention are readily applicable to other architectural, civil engineered or structural engineered structures. For example, in another application, the structure 10 shown in FIG. 17 is a tower-type structure such as a radio tower, a tower for high voltage lines, a tower for supporting a tram, a water tower, a refinery tower, a tower of a suspension bridge, a smoke stack, etc. and the support base 20 is the foundation supporting the tower or smoke stack. In another application, the structure 10 is a bridge and the support base 20 is the foundation and ground supporting the bridge. In yet another application, the structure 10 is a dam and the support base 20 is the ground supporting the dam. In yet another application, the structure 10 is an above-ground pipeline for carrying hydrocarbons, chemicals, water, etc. and the support base 20 is the foundation and ground supporting the pipeline. In yet another application, the structure 10 is an above-ground tank for storing hydrocarbons, chemicals, water, etc. and the support base 20 is the foundation and ground supporting the tank. In one application, the structure 10 is the framework of a roller coaster, Ferris wheel or other amusement park ride and the support base 20 is the foundation and ground supporting the ride.

As can be easily understood, the method and system of the subject invention is readily applicable to equipment structures. For example, in one application, the structure 10 illustrated in FIG. 17 is a drilling tower/derrick, helicopter platform, crane, or other structure supported off of an offshore oil platform, and the support base 20 is the platform itself. In another application, the structure 10 is the boom of a crane and the support base 20 is the superstructure of the crane. In one application, the structure 10 is the pedestal supporting the superstructure of a marine pedestal-type crane and the support base 20 is the ship, dock or oil well platform supporting the pedestal of the crane. In one application, the structure 10 is the boom of a tower crane such as those utilized in the construction of high-rise buildings and the support base 20 is the mast of the tower crane. In one application, the structure 10 is the mast of a tower crane and the support base 20 is the building or foundation supporting the tower crane. In yet another application, the structure 10 is a wing and the support base 20 is the fuselage from which the wing extends.

It should be understood that the method and system of the subject invention are readily applicable to a wide variety of structures and that the aforementioned structural applications are only provided as examples. Thus, they are not to be used or considered to limit the breadth of the invention.

As indicated in FIGS. 17 and 18, a series of motion sensors 25 are coupled to the structural framework 15 of the structure 10 at different locations on the structure 10 [block 100]. A system 5 for monitoring the structural integrity of the structure 10 is formed by placing the sensors 25 in operable communication with a CPU 30 [block 105].

In one embodiment, where it is only necessary or desired to track the overall structural change (e.g., degradation) of the structure 10, a minimal number of sensors 25 will be located at regular intervals along the length or height of the structure. For example, where the structure 10 is a building or tower, one or more sensors 25 will be located on each floor or every other floor.

On the other hand, in one embodiment, where it is necessary or desired to be able to identify specific locations of structural change (e.g., degradation), a greater number of sensors 25 will be located throughout the structure. For example, where the structure 10 is a building or tower, a sensor might be located at each junction joining individual structural members forming the building or tower.

In one embodiment where the structure 10 is a building, the sensors 25 may be located internal or external to the walls of the buildings. Also, the sensors 25 may be installed at the time of building construction or after the building is built as part of a retrofit project.

During a first period of structural excitation, each motion sensor 25 provides first motion readings (see FIG. 3) to the CPU 30 [block 110]. The first motion readings, through the deconvolution process described in the preceding Sections, are analyzed to separate the first structural response of the structure 10 from the effects of the excitation and the coupling of the structure 10 to the support base 20 (see FIGS. 4-7) [block 115]. The first structural response (e.g., the structure's first shear velocity and first attenuation characteristics) are stored in the CPU 30 [block 120].

During a second period of structural excitation, each motion sensor 25 provides second motion readings (see FIG. 3) to the CPU [block 125]. The second motion readings, through the deconvolution process, are analyzed to separate the second structural response of the structure 10 from the effects of the excitation and the coupling of the structure 10 to the support base 20 (see FIGS. 4-7) [block 130]. The second structural response (e.g., the structure's second shear velocity and second attenuation characteristics) are compared to the first structural response [block 135]. A difference between the two structural responses indicates that the structure 10 has changed (e.g., degraded) during the period between the first and second excitations.

Figure 19:
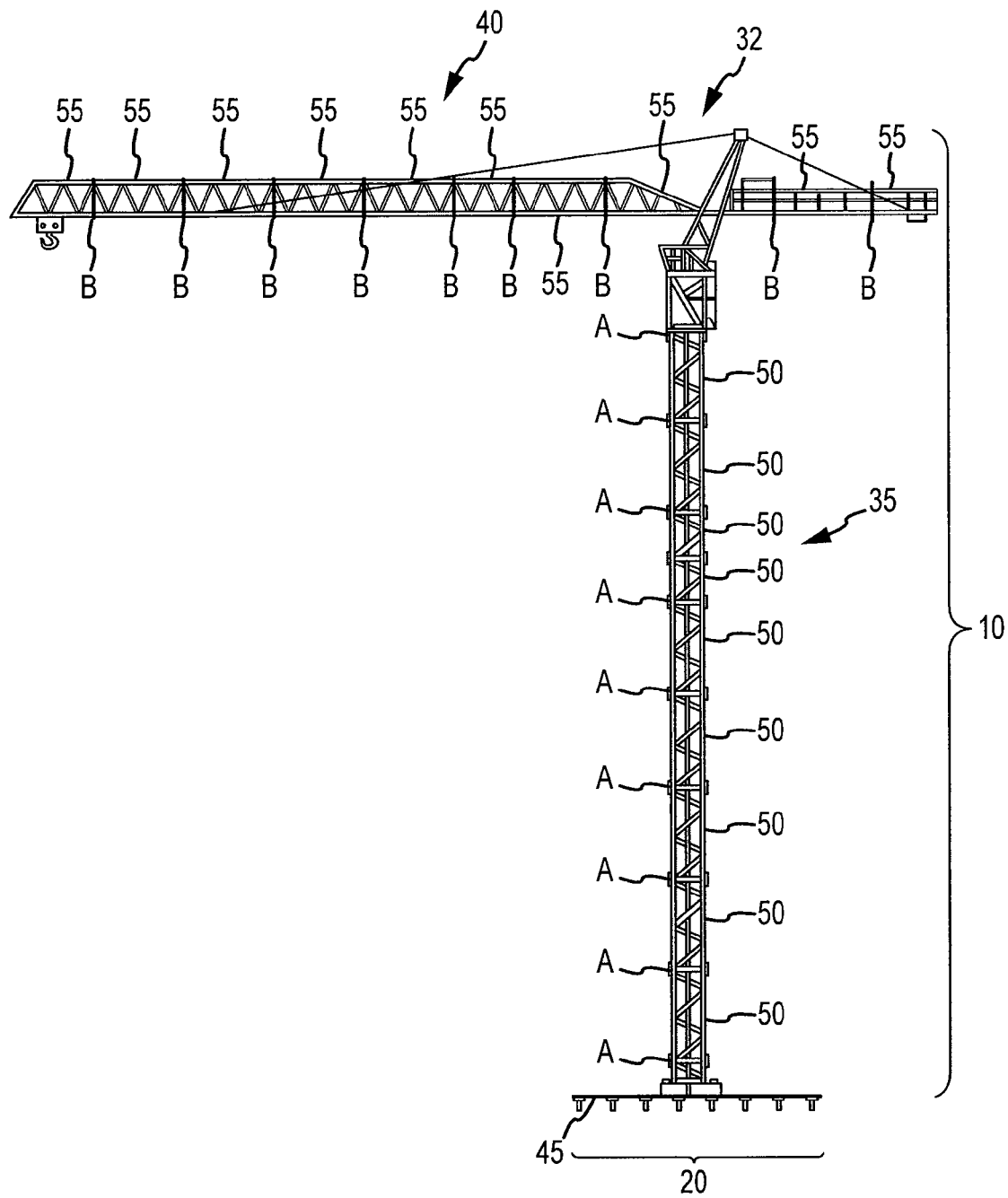
FIG. 19 is an elevation of a structure (i.e., a tower crane), wherein the structure to be analyzed is the crane mast and boom and the support base is the ground.
Figure 20:
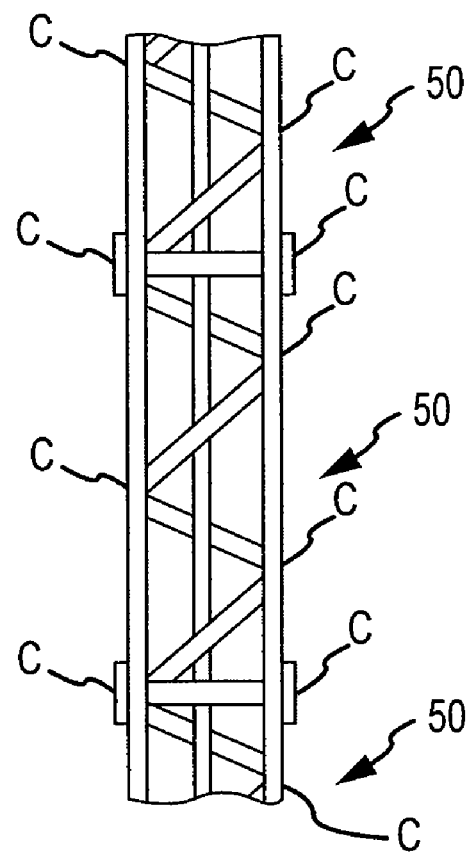
FIG. 20 is an enlarged view of a typical section of the crane mast.
Figure 21:
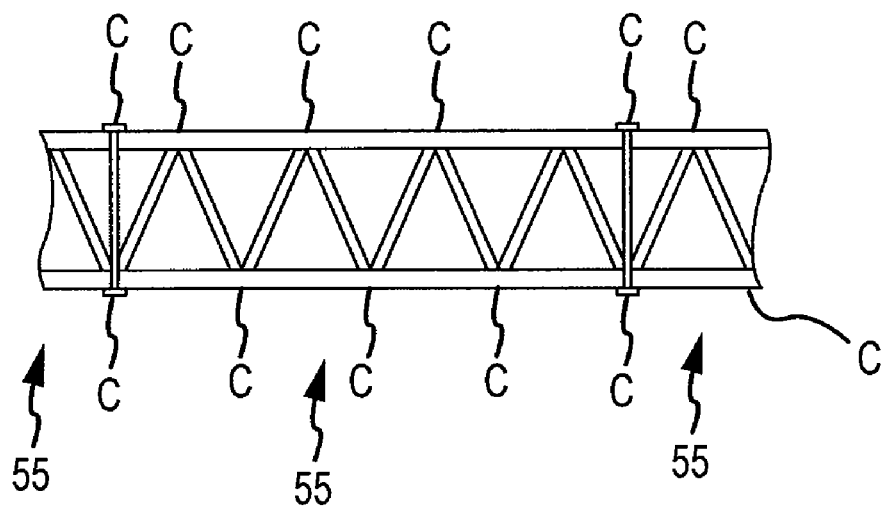
FIG. 21 is an enlarged view of a typical section of the crane boom.
Figure 22:
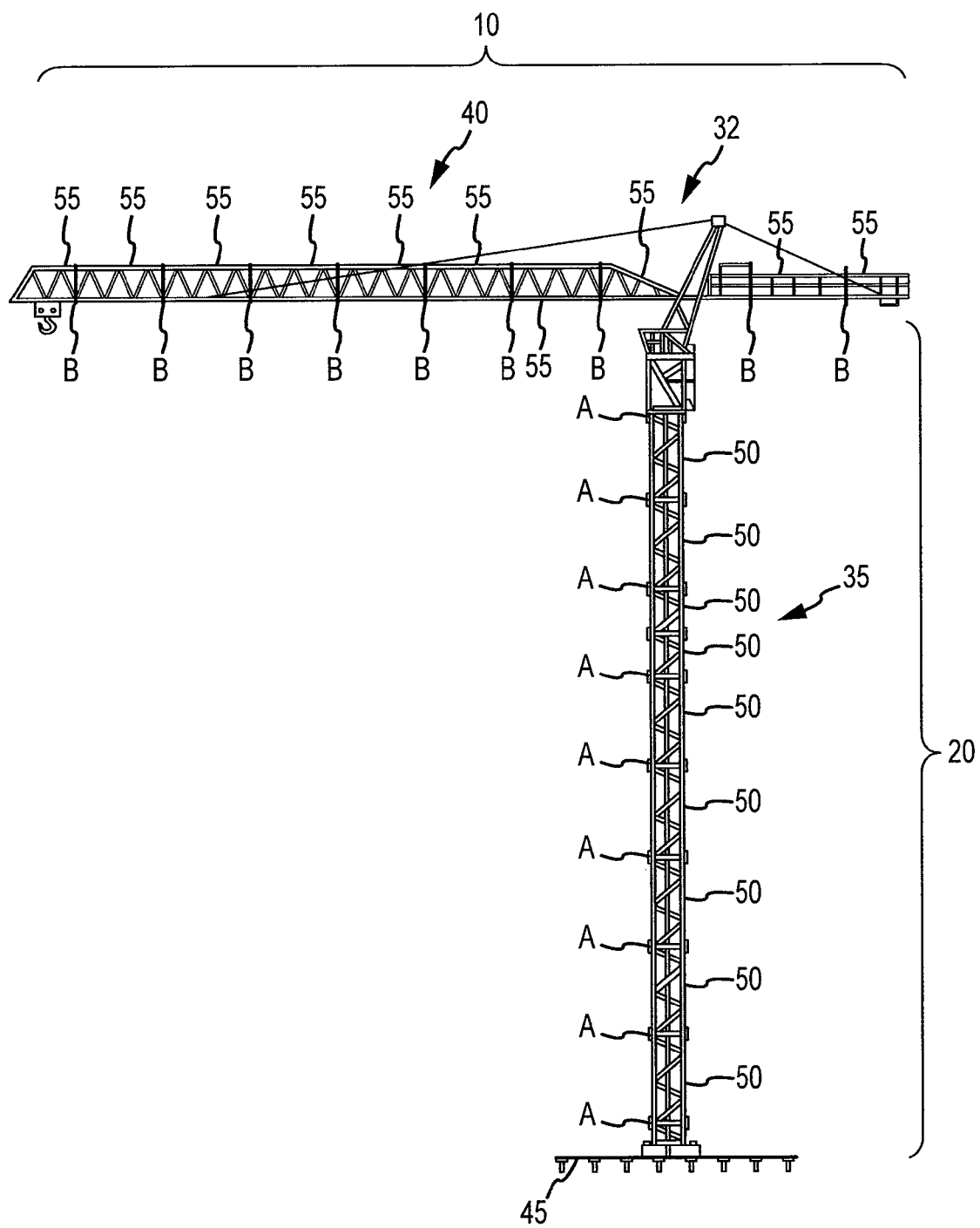
FIG. 22 is an elevation of the same tower crane depicted in FIG. 15, except the structure to be analyzed is the crane boom and the support base is the crane mast and the ground.
Figure 23:
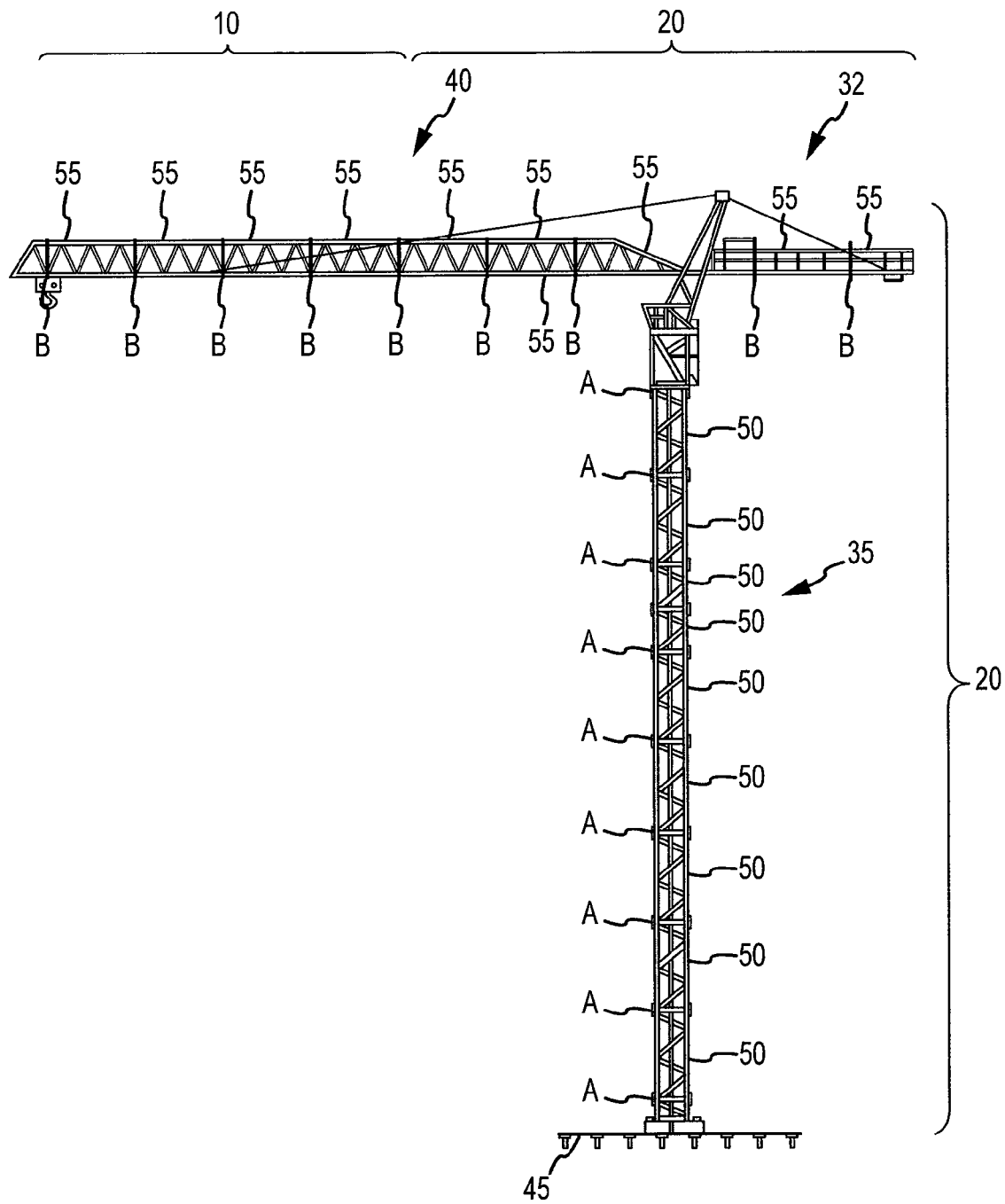
FIG. 23 is an elevation of the same tower crane depicted in FIG. 15, except the structure to be analyzed is the distal third of the crane boom and the support base is the proximal two thirds of the crane boom, the crane mast and the ground.

For an example illustration of how parts or sections of a structure 10 can be analyzed separately from the rest of the structure 10 to determine the structural change (e.g., degradation) of said parts or sections or to identify specific locations of structural change, reference is now made to FIGS. 19-23. FIG. 19 is an elevation of a structure 10 (i.e., a tower crane 32), wherein the structure 10 to be analyzed is the crane mast 35 and boom 40 and the support base 20 is the ground 45. FIG. 20 is an enlarged view of a typical section 50 of the crane mast 35. FIG. 21 is an enlarged view of a typical section 55 of the crane boom 40. FIG. 22 is an elevation of the same tower crane 32 depicted in FIG. 19, except the structure 10 to be analyzed is the crane boom 40 and the support base 20 is the crane mast 35 and the ground 45. FIG. 23 is an elevation of the same tower crane 32 depicted in FIG. 19, except the structure 10 to be analyzed is the distal third of the crane boom 40 and the support base 20 is the proximal two thirds of the crane boom 40, the crane mast 35 and the ground 45.

As can be understood from FIGS. 17 and 19, in one embodiment, the system 5 includes a CPU 30 in communication with sensors 25 located at the junctions A between each mast section 50 and the junctions B between each boom section 55. Such a sensor arrangement allows the structural degradation to be determined for the overall crane 32 and for major elements of the crane 32 such as the mast 35 and boom 40.

In another embodiment, as can be understood from FIGS. 20 and 21, the sensors 25 are located at the junctions C between each structural element forming a mast section 50 and a boom section 55. Such a sensor arrangement allows the structural degradation of the crane 32 to be pinpointed to a specific structural element or group of elements by decoupling the structural response for a mast or boom section 50, 55 in question from the rest of the crane 32 as can be understood from the method discussed in relation to FIGS. 19, 22 and 23.

As shown in FIG. 19, the crane 32 is the structure 10 for which a first structural response is to be determined and the ground 45 is the support base 20 to which the crane 32 is coupled. The crane 32 is subjected to a structural excitation (e.g., a weight is suddenly released from the boom 40 to cause a tolerable amount of whip in the boom 40 and the mast 35) and the sensors 25 provide their motion readings to the CPU 30. Through the deconvolution methods described in the preceding Sections, the first structural response of the crane 32 is decoupled from the effects of the excitation and the coupling of the crane 32 to the ground 45 (i.e., the support base 20). The first crane structural response is compared to a later obtained crane structural response to determine if the crane's structure has changed (e.g., degraded) over the period in question.

As indicated in FIG. 22, the boom 40 is the structure 10 for which a first structural response is to be determined and the mast 35 and the ground 45 are the support base 20 to which the boom 40 is coupled. The boom 40 is subjected to a structural excitation in the manner already described. Through deconvolution, the first structural response of the boom 40 is decoupled from the effects of the excitation and the coupling of the boom 40 to the support base 20 (i.e., the mast 35 and ground 45). The first boom structural response is compared to a later obtained boom structural response to determine if the boom's structure has changed (e.g., degraded) over the period in question.

As indicated in FIG. 23, the distal third of the boom 40 is the structure 10 for which a first structural response is to be determined and the proximal two thirds of the boom 40, the mast 35 and the ground 45 are the support base 20 to which the distal third of the boom 40 is coupled. The boom 40 is subjected to a structural excitation in the manner already described. Through deconvolution, the first structural response of the distal third of the boom 40 is decoupled from the effects of the excitation and the coupling of the distal third of the boom 40 to the support base 20 (i.e., the proximal two thirds of the boom 40, the mast 35 and ground 45). The first boom structural response for the distal third of the boom 40 is compared to a later obtained boom structural response for the distal third of the boom 40 to determine if the boom's structure has changed (e.g., degraded) over the period in question.

As can be understood, depending on the number and location of the sensors on the crane 32, structural responses can be determined for ever smaller portions of the crane 32. Thus, with an adequate number of sensors, structural degradation of a specific portion of the crane 32 could be determined by employing deconvolution.

In summary, the motion of a structure 10 during a period of excitation is a function of the three following components: (1) the excitation experienced by the structure 10; (2) the coupling of the structure 10 to its support base 20; and (3) the structural response of the structure itself (i.e., the structure's mechanical properties such as the rate at which shear waves propagate through the structure and the structure's ability to attenuate the wave energy resulting from an excitation). The structural response of the structure 10 is independent of the excitation and base coupling. Therefore, changes in the structural integrity of a structure 10 may be identified by comparing a first structural response to a later structural response.

To obtain the first structural response, the motion of the structure 10 is recorded during a first excitation period. The motion data for the first excitation period is deconvoluted to separate the structural response component from the other two components of the structural motion, namely, the excitation and the coupling components. The first structural response is stored.

The motion of the structure 10 is recorded during a second excitation period. The motion data for the second excitation period is deconvoluted to separate the structural response component form the other two components of the structural motion (i.e., the excitation and coupling components). The second structural response is compared to the first structural response. A difference between the two structural responses indicates a change in structural integrity for the structure 10.

X. A System and Method of Monitoring Pipeflow.

As explained in the preceding Sections of this Detailed Description in more detail, the motion of a structure (e.g., a fluid conduit such as a pipe) during a period of excitation is a function of the following components or effects: the excitation experienced by the structure; the coupling of the structure to its support base (e.g., the ground in the context of a pipe in a refinery or pipeline, or a drilling rig in the context of a drilling fluid pipe extending though a borehole); and the structural response (i.e., the mechanical properties) of the structure. At least two mechanical properties that are of interest include the rate at which shear waves propagate through the structure (i.e., the structure's shear velocity) and the structure's ability to attenuate the wave energy resulting from an excitation (i.e., the structure's attenuation).

By deconvolving the motion recorded at different locations within or on the structure (e.g., at different pipe segments or lengths in the context of a pipe), it is possible to separate the structural response of the structure from the effects of the excitation experienced by the structure and the coupling of the structure to its base support. The structural response of the structure is dependent on the structure's mechanical properties and is independent of the excitation experienced by the structure and the coupling of the structure to its base support. Thus, it is possible to monitor the structural response or characteristics (e.g., structural integrity, change in density associated with a structure, etc.) of a structure, such as a pipe, over a period of time by employing the methodology discussed in the preceding Sections.

As discussed in the immediately preceding Section of this Detailed Description, the excitation experienced by the structure can result from a variety of natural or non-natural events. In the context of a pipe, events that can cause the pipe to experience excitation include impact forces (e.g., a body impacting the pipe or near the pipe, the pipe impacting the wall or casing of a borehole, etc.), the flow of fluid (e.g., drilling fluid) through the pipe, and vibrations generated by pumps and other mechanical equipment that are connected to the pipe.

Figure 24:
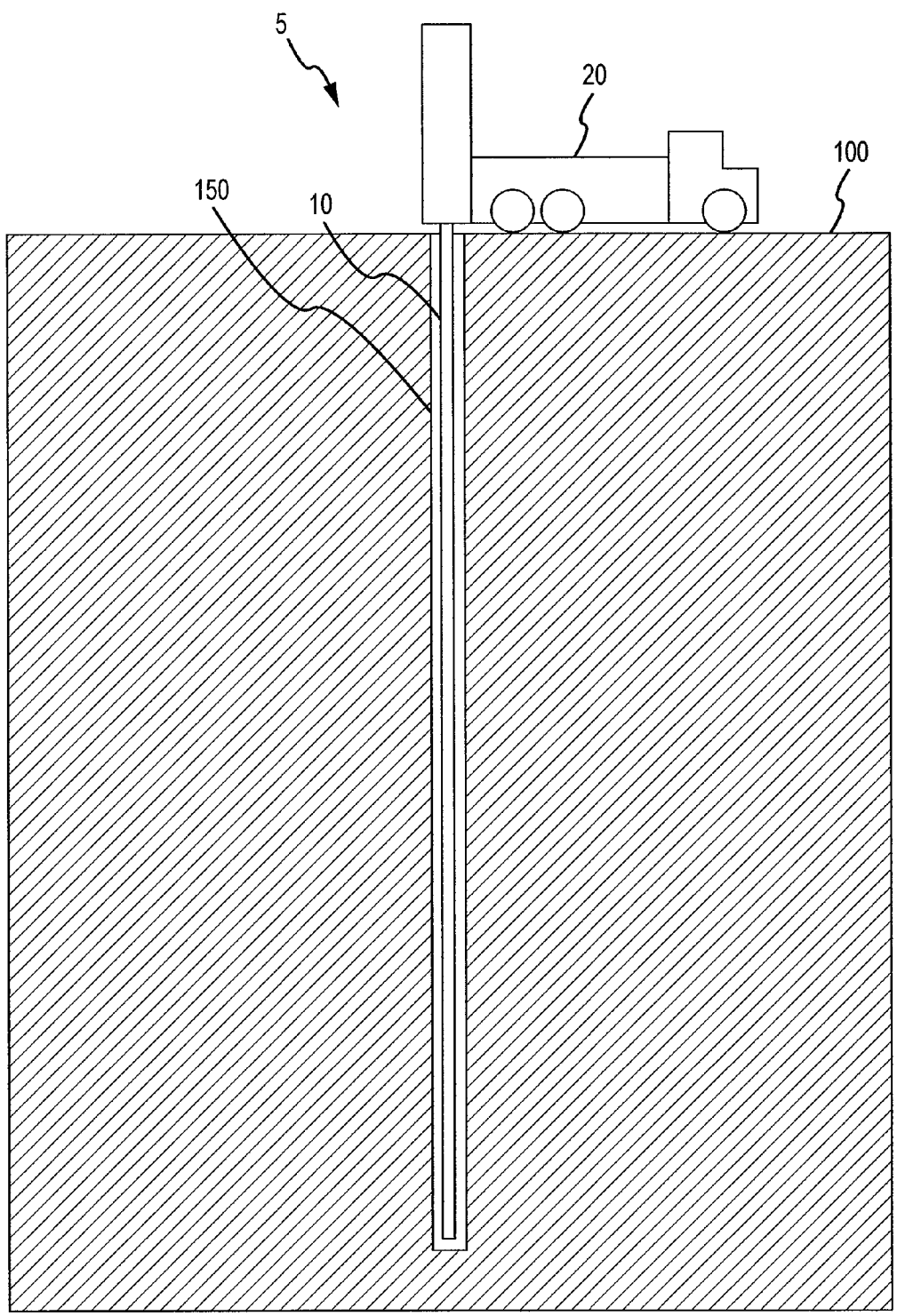
FIG. 24 is a diagrammatic representation of a system employing the method of the subject invention, wherein a pipe (i.e., the structure) extends through the ground via a borehole and is coupled to a drilling rig (i.e., the support base).
Figure 25:
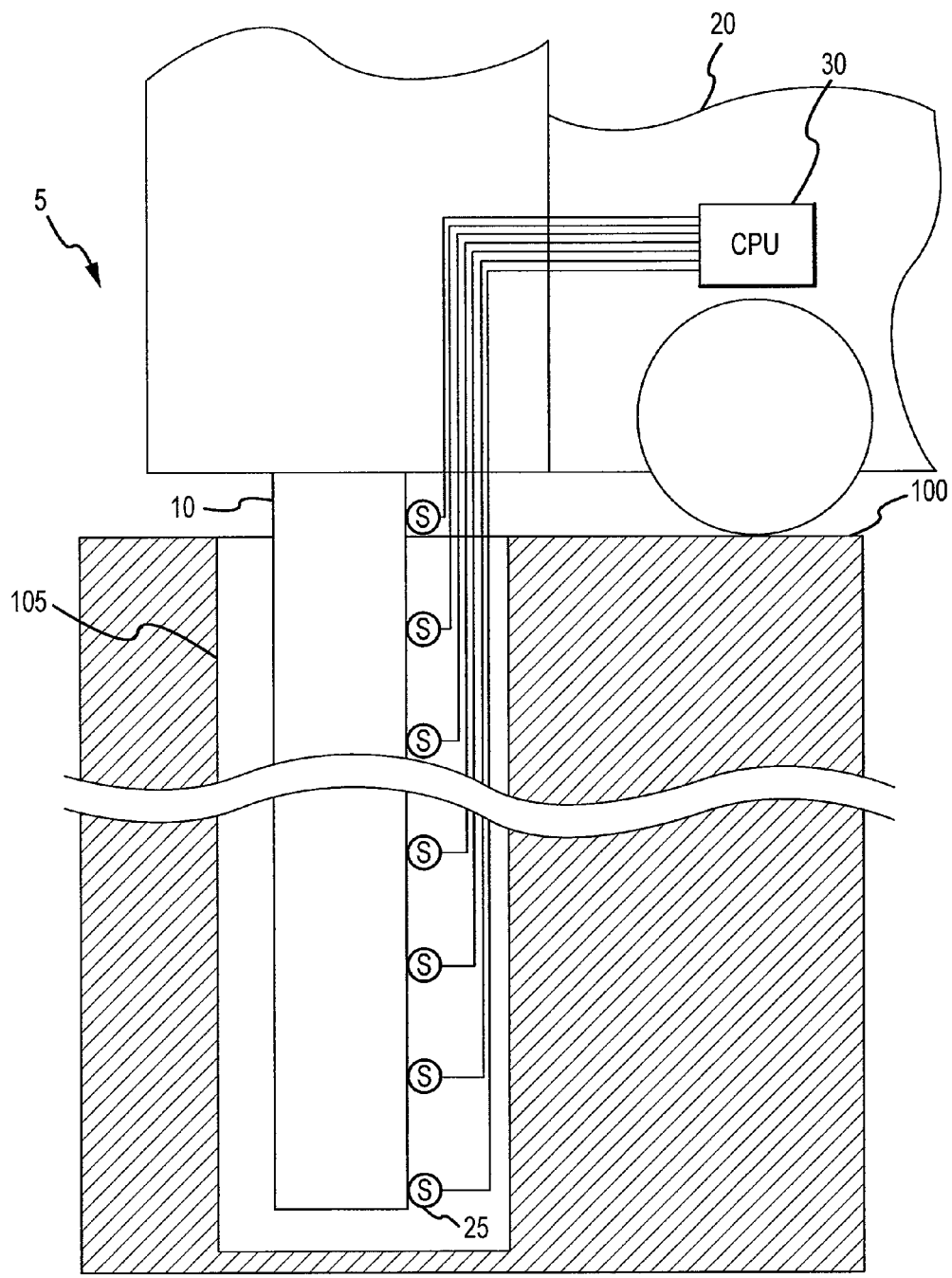
FIG. 25 is an enlarged view of the system depicted in FIG. 24.
Figure 26:
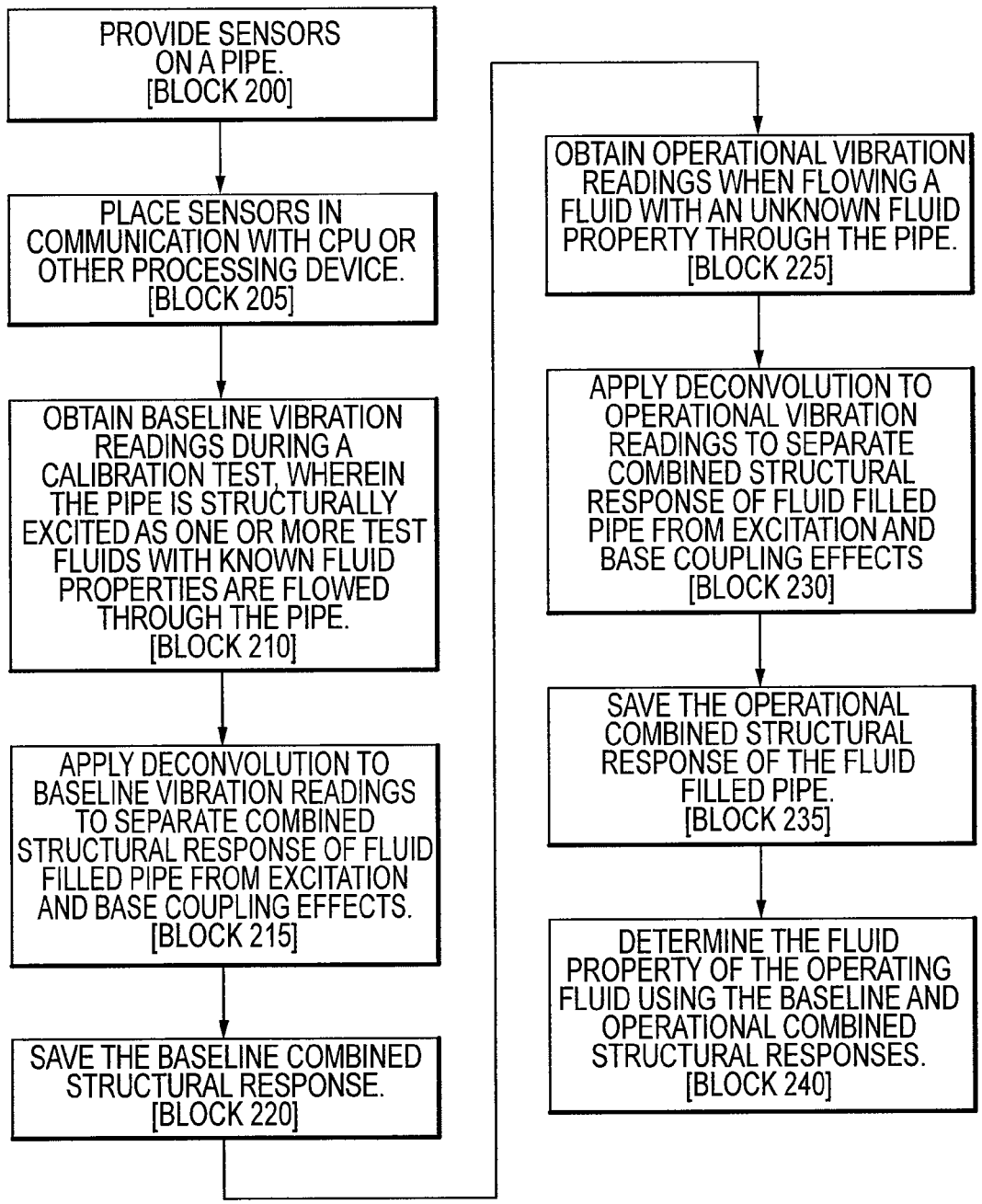
FIG. 26 is a block diagram outlining the method of the subject invention depicted in FIGS. 24 and 25.

As discussed in the immediately preceding Section of this Detailed Description, the method and system described above in more detail are readily applicable to a wide variety of applications. For example, in one application, the system and method may be employed to monitor a fluid flow through a fluid conveying pathway 10, for example, an open channel, closed conduit, etc. (referred to generically as a pipe throughout the rest of this document), to determine and monitor one or more characteristics of the fluid flow (e.g., the mass-density of the fluid). For a discussion of such a system and method, reference is now made to FIGS. 24-26. FIG. 24 is a diagrammatic representation of a system 5 employing the method to monitor the fluid-density of a fluid flow through a pipe 10. FIG. 25 is an enlarged view of the system 5 depicted in FIG. 24. FIG. 26 is a block diagram outlining the method to monitor the fluid-density of a fluid flowing through the pipe 10.

As depicted in FIG. 24, in one embodiment, a pipe 10, which may convey drilling fluid, is the structure 10 to be analyzed. The pipe 10 extends through a borehole 105 in the ground 100. A drilling rig serves as the support base 20 for the pipe 10. A system 5 for monitoring the flow of fluid through the pipe 10 is used to determine and monitor the mass-density of the fluid, such as drilling fluid, injected into or pumped out of the borehole 105 via the pipe 10. Among other benefits, such monitoring and determining of the mass density of a fluid in the pipe 10 may allow for the mass-density of the fluid to be modified during an operation involving the fluid. For example, the density of drilling fluid may need to be modified to remain within a certain range during the drilling operation because the borehole may collapse if the density of the drilling fluid is too low, and the drilling fluid may undesirably fracture the ground surrounding the borehole or damage a casing positioned in the borehole if the density is too high.

As indicated in FIGS. 25 and 26, a series or array of motion sensors 25 are coupled along the length of the pipe 10 at different locations on the pipe 10 [block 200]. The system 5 for monitoring the flow of fluid through the pipe 10 is formed by placing the sensors 25 in operable communication with a CPU 30 [block 205] or other suitable processing device. The sensors 25 may be placed in operable communication with the CPU 30 using any suitable means, including, but not limited to, wired or wireless communication, or some combination thereof. In some embodiments, the sensors 25 will be accelerometers or other types of motion sensors, and the sensors 25 will be mounted on an exterior surface of the pipe 10. In some embodiments, relatively few sensors 25 may be located along the length of the pipe 10. In other embodiments, the sensors 25 may be provided in greater numbers, for example, on each pipe segment/length or on each pipe coupling/joint.

Motion sensors 25 placed on the pipe 10 can be used to extract the propagation of flexural modes of the pipe 10, or modes in the wall of the pipe 10, that propagate between sensors 25 placed along of the pipe 10. The ambient noise generated in the extended pipe assembly by pumps and other mechanical equipment helps to extract the desired signals. Specifically, the noise acts to structurally excite the pipe 10.

Via the array of sensors 25, it is possible to discriminate between waves propagating in different directions, thereby boosting the signal to noise ratio. The array techniques can be used to directly measure the phase and/or group velocity of the modes that propagate along the pipe 10. By placing sensors 25 along the circumference of the pipe, it is possible to separate the different modes of the pipe 10 more effectively. Cross-correlation and/or deconvolution can be used to separate the structural response or characteristics of a fluid filled pipe from the effects of the excitation experienced by the fluid filled pipe and the coupling of the fluid filled pipe to its base.

The noise from pumps and other mechanical equipment structurally excites the fluid filled pipe 10, causing vibrations in it. The vibrations of the fluid filled pipe 10, more specifically, the structural response or characteristics of the fluid filled pipe, which shall be referred to as the "combined structural response" or "combined structural characteristics," are a result of: (1) the mechanical properties of the pipe 10; and (2) the properties of the fluid inside the pipe 10, for example, the viscosity and, especially, the density of the fluid. Deconvolution can be utilized to separate the combined structural response or characteristics of the fluid filled pipe 10 from the effects of the excitation experienced by the fluid filled pipe 10 and the coupling of the fluid filled pipe 10 to its support base.

The combined structural response of the fluid filled pipe 10 at a point in time can be compared to a combined structural response of the fluid filled pipe 10 at other points in time. Assuming that the pipe structural response (e.g., the pipe mechanical properties) is the same at both points in time, or that any change is negligible, any similarity in the combined structural responses indicates that the fluid properties at the compared times are similar, and any difference in the combined structural response will result from a change in the properties of the fluid flowing through the pipe 10. If the fluid properties of a fluid flowing through the pipe 10 are known at one of the points in time, the fluid properties of a fluid flowing through the pipe 10 can be estimated, calculated or otherwise determined for the other points in time.

The relation between the velocity of wave propagation in the pipe 10 and the fluid density can be calibrated by performing calibration testing to obtain a baseline motion for the pipe 10 when a fluid is pumped therethrough. Specifically, the sensors 10 supply vibration readings to the CPU 30 during the calibration testing, wherein the pipe 10 is structurally excited as one or more test fluids are each pumped through the pipe 10 [block 210]. Each test fluid may be pumped through the pipe 10 at various known densities to obtain baseline vibration or motion readings for the pipe 10 at different densities for each test fluid. For example, a drilling fluid may be pumped through the pipe at different densities and the pipe vibration or motion monitored and recorded to establish baseline motion readings for the pipe 10. Alternatively, to arrive at a baseline vibration or motion for the pipe 10 at different mass-densities for a fluid, numerical modeling may be utilized to find the waves that propagate along the fluid-filled pipe 10 as a function of the mass-density of the fluid.

Deconvolution or cross-correlation may be applied to the baseline vibration or motion readings to separate the combined structural response of the fluid filled pipe for each baseline vibration or motion reading from the effects of the excitation experienced by the fluid filled pipe 10 and the coupling of the fluid filled pipe 10 to its base support [block 215]. Each resulting baseline combined structural response of the fluid filled pipe for the one or more test fluids at one or more densities may be saved for comparison to a combined structural response of the fluid filled pipe 10 during flowing an operational fluid (e.g., drilling fluid, etc.) through the pipe 10 [block 220]. The baseline combined structural responses may be saved in a table, graph or other convenient format for later retrieval. The baseline combined structural responses may also be used to develop mathematical or empirical equations or formulas that predict or estimate the combined structural response for the pipe 10 as a function of fluid density flowing through the pipe 10.

When an operating or operational fluid is flowed (e.g., by pumping) through the pipe 10, for example, during drilling operations by a drill rig 20 joined to the pipe 10, the sensors 25, which may be the same sensors used during calibration testing or different sensors, relay the resulting vibrations of the pipe 10 to the CPU 30 [block 225] or other suitable processing unit, which may be the same CPU or other processing unit used during calibration testing or a different unit. Depending on the embodiment, the sensors relay the vibrations intermittently or generally continuously. When the vibrations are relayed generally continuously, the fluid density can be monitored generally continuously. Deconvolution or cross-correlation is applied to the sensor readings taken while flowing an operating fluid through the pipe 10 to separate the operational combined structural response of the fluid filled pipe 10 from the effects of the excitation experienced by the fluid filled pipe 10 and the coupling of the fluid filled pipe 10 to its base support (e.g., the drill rig 20) [block 230].

The resulting operational combined structural response of the fluid filled pipe may be saved for comparison to the baseline combined structural response [block 235]. The vibrations or, more specifically, the operational combined structural responses of the fluid filled pipe obtained during drilling or other operations are compared to the baseline combined structural responses obtained during the calibration test for the pipe 10 to estimate, calculate or otherwise determine the fluid density of the fluid [block 240]. Specifically, in one embodiment, the waves that propagate between the sensors 25 during operations, as obtained from cross-correlation or deconvolution, can be compared with the waves recorded from the calibration testing or numerical simulation, as also obtained from cross-correlation or deconvolution, to estimate the mass-density of the operational fluid. In other embodiments, the operational combined structural responses for an operational fluid in the pipe 10 may be compared to tabulated values for the baseline combined structural responses of the pipe 10 to estimate or otherwise determine the fluid density for the operational fluid. As needed, the fluid density for the operational fluid in a pipe 10 may be estimated or otherwise determined by interpolating or extrapolating from the baseline combined structural responses for the pipe 10. In yet other embodiments, equations or other formulas based on the baseline combined structural responses for the pipe 10 may be solved using the operational combined structural responses for an operational fluid flowing in the pipe 10 to estimate or otherwise determine the fluid density for the operational fluid.

Any of the foregoing methods, or any other appropriate method, for determining the fluid density of a operational fluid by use of the baseline combined structure response may be facilitated with the use of a computer or other suitable computational device. Further, two or more of the foregoing methods, or any other appropriate method, may be used concurrently to develop an estimation or other calculation of the fluid density for an operational fluid in a pipe 10. Yet further, the underlying data or information for obtaining the baseline structural combined responses may be obtained from computer modeling of the vibrations that occur when a fluid flows in the operational fluid filled pipe, from sensing and recording the vibrations from flowing one or more types of fluids with known fluid properties in the operational fluid filled pipe, from sensing and recording the vibrations from flowing one or more types of fluids with known fluid properties in a fluid pipe having similar properties to the operational fluid filled pipe, or from some combination thereof. Still yet further, the fluid used in the computer modeling or calibration testing to obtain the underlying data or information for the baseline combined structural response may be the same type of fluid used in the operational fluid filled pipe (e.g., the calibration and operational fluid are both drilling fluids) or a different type of fluid (e.g., the calibration fluid is water and the operational fluid is a drilling fluid).

The preceding example depicted in FIGS. 24-26 is given in the context of flowing a drilling fluid through a pipe 10 extending into a borehole 105 during drilling operations by a drilling rig 20. However, the above-described system and method is not limited to such an embodiment. For example, in other embodiments, the pipe 10 conveying the drilling fluid may be located outside the borehole 105, for example, on or above the surface of the ground 100. Depending on the embodiment, the sensors will be located on the pipe in the borehole or on the pipe outside the borehole as the pipe extends along or above the ground surface.

In other embodiments, the operation is not a drilling operation and the fluid being monitored is not a drilling fluid. Instead, the operation is a refinery, the pipe is a refinery pipe or pipeline, and the fluid being monitored for fluid density or another fluid property is a refinery fluid such as oil, gasoline, diesel fuel, asphalt, etc. The system and method could also be applied to chemical plants, manufacturing plants, coal slurry pipelines, waste treatment plants, nuclear reactors, etc. Applying the system and method to such operations would allow process controls to determine if, for example, a fluid density became too high/low or if the pipe has run dry such that a pumping system should shut down.

Furthermore, in addition to being able to monitor the fluid density of a fluid flowing through a pipe, the system and method described above for monitoring and/or determining fluid density can also be used to monitor and/or determine fluid viscosity or any other fluid property that has a measurable effect on the propagation of waves in pipes. Also, the system and method could be used to detect the formation of bubbles (gas) in a fluid flow.

The method and system described above may further be used to estimate one or more fluid properties, such as fluid density or fluid viscosity, for fluids flowing through pipes and piping systems that are similar structurally and mechanically to a pipe or pipe system calibrated as described above. More specifically, vibrations in a fluid filled pipe or piping system may be measured by sensors and recorded while flowing one or more fluids with a known fluid property, such as fluid density, through the fluid filled pipe or piping system. Each recorded vibration may be cross-correlated or deconvoluted to separate a baseline combined structural response from the effects of the excitation experienced by the fluid filled pipe or pipe system and the coupling of the fluid filled pipe or pipe system to its base.

Vibrations in a second fluid filled pipe or piping system, with similar structural and mechanical properties to the baseline fluid filled pipe or pipe system, may be measured by sensors and recorded while flowing a fluid through the second fluid filled pipe or piping system. Each recorded vibration for this second fluid filled pipe or piping system may be cross-correlated or deconvoluted to separate a combined structural response from the effects of the excitation experienced by the second fluid filled pipe or pipe system and the coupling of the second fluid filled pipe or pipe system to its base. The combined structural responses from the second fluid filled pipe or pipe system may be compared to the baseline combined structural responses for the baseline fluid filled pipe or piping system, in a manner similar to the one described above for comparing the baseline combined structural responses of a pipe to the pipe's operational combined structure responses, to estimate, calculate or otherwise determine a fluid property, such as fluid density, of the fluid flowing through the second fluid pipe or piping system.

In summary, sensors take a baseline vibration reading along a pipe when one or more test fluids with well known values for the fluid property being measured (e.g., fluid density, fluid viscosity and so on) are flowed through the pipe during a calibration period. The baseline vibration readings are analyzed via cross-correlation and/or deconvolution to separate the baseline combined structural response of the fluid filled pipe from the effects of the excitation experienced by the fluid filled pipe and the coupling of the fluid filled pipe to its base. The baseline structural response is stored. During field or other operations, sensors take vibrational readings along the pipe (or a pipe with structural and mechanical properties similar to the structural and mechanical properties of the baseline/calibrated pipe) when an operational or operating fluid (e.g., drilling fluid) is flowed through the pipe (or a pipe or pipe system with similar structural and mechanical properties to the baseline/calibrated pipe or pipe system). The operational vibration readings are analyzed via cross-correlation and/or deconvolution to separate the operational combined structural response of the fluid filled pipe from the effects of the excitation experienced by the fluid filled pipe and the coupling of the fluid filled pipe to its base. The operational combined structural response is stored. The baseline and operational structural responses are compared, and the similarities or differences in the structural responses are used to determine the fluid properties (e.g., fluid density, fluid viscosity and so on) of the operational fluid.

It should be noted that all directional references set forth herein (e.g., upper, lower, upward, downward, left, right, leftward, rightward, top, bottom, above, below, vertical, horizontal, clockwise, and counterclockwise) are relative and only used for identification purposes to aid the reader's understanding of the embodiments of the present invention, and are not limitations, particularly as to the position, orientation, or use of the invention unless specifically set forth in the claims. References to any joinder of elements (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

I claim:

1. A method of determining a value for a fluid property of a fluid flowing through a fluid conduit, further the method comprising:

obtaining a first vibration reading for a fluid conduit when a fluid flows through the fluid conduit;

subjecting the first vibration reading to at least one of deconvolution and cross-correlation to separate a first combined structural response of the fluid conduit for the first vibration reading from excitation and base coupling effects for the first vibration reading;

determining a value of a fluid property for the fluid by using the first combined structural response of the fluid conduit and a second combined structural response for a second vibration reading;

obtaining the second vibration reading when a second fluid conduit, with mechanical properties similar to mechanical properties of the fluid conduit, contains a second fluid with the fluid property known; and subjecting the second vibration reading to at least one of deconvolution and cross-correlation to separate the second combined structural response for the second vibration reading from excitation and base coupling effects for the second vibration reading.

2. The method of claim 1, wherein the step of obtaining the second vibration reading comprises using a sensor positioned on the second fluid conduit to obtain the second vibration reading.

3. The method of claim 1, wherein the fluid and the second fluid are different types of fluids.

4. The method of claim 1, wherein the fluid and the second fluid are a same type of fluid.

5. The method of claim 4, wherein the same type of fluid comprises a drilling fluid.

* * * * *